United States Patent
Blum et al.

(10) Patent No.: US 10,076,406 B2
(45) Date of Patent: Sep. 18, 2018

(54) LAYERED MEDICAL DEVICE WITH IMPROVED ADHESION AND METHODS OF MAKING

(71) Applicant: COOK MEDICAL TECHNOLOGIES LLC, Bloomington, IN (US)

(72) Inventors: Kevin Blum, Lanesville, IN (US);
Keith Milner, West Lafayette, IN (US);
Sara Marie Sherman, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/979,770

(22) Filed: Dec. 28, 2015

(65) Prior Publication Data

US 2016/0184080 A1 Jun. 30, 2016

Related U.S. Application Data

(60) Provisional application No. 62/098,871, filed on Dec. 31, 2014.

(51) Int. Cl.
*A61F 2/07* (2013.01)
*A61F 2/89* (2013.01)
(Continued)

(52) U.S. Cl.
CPC ............... *A61F 2/07* (2013.01); *A61F 2/89* (2013.01); *A61L 31/04* (2013.01); *A61L 31/088* (2013.01);
(Continued)

(58) Field of Classification Search
CPC ........ A61F 2/07; A61F 2002/072; A61F 2/89; A61F 2210/0076; A61L 31/088;
(Continued)

(56) References Cited

U.S. PATENT DOCUMENTS 5,628,788 A * 5/1997 Pinchuk .................... A61F 2/07
606/194
7,799,261 B2 9/2010 Orr et al.
(Continued)

FOREIGN PATENT DOCUMENTS

| WO | WO 01/15751 A1 | 3/2001 |
| WO | WO 2009/026086 A2 | 2/2009 |
| WO | WO 2010/107545 A2 | 9/2010 |

OTHER PUBLICATIONS

Young, "Overview of Sol-Gel Science and Technology" Army Research Laboratory, (Jan. 2002).*
(Continued)

*Primary Examiner* — Paul Prebilic
(74) *Attorney, Agent, or Firm* — Brinks Gilson & Lione

(57) ABSTRACT

An endoluminal prosthesis for placement within a body vessel may include a tubular support structure including a proximal end segment, a distal end segment, an intermediate segment positioned between the proximal end segment and the distal end segment, a lumen extending longitudinally within the support structure, a luminal surface, and an abluminal surface opposite the luminal surface. The prosthesis may include a first layer of nonwoven electrospun fibers positioned on the luminal surface of the support structure. The prosthesis may include a second layer of nonwoven electrospun fibers positioned on the abluminal surface of the support structure. At least one of the proximal end segment or the distal end segment of the support structure may be encapsulated within a covering including the first layer of nonwoven electrospun fibers and the second layer of nonwoven electrospun fibers. The intermediate segment of the support structure may be unencapsulated within the covering.

18 Claims, 12 Drawing Sheets

(51) Int. Cl.
   *B29C 47/00* (2006.01)
   *A61L 31/04* (2006.01)
   *A61L 31/08* (2006.01)
   *B29L 9/00* (2006.01)

(52) U.S. Cl.
   CPC .. *B29C 47/0021* (2013.01); *A61F 2210/0076* (2013.01); *B29L 2009/00* (2013.01)

(58) Field of Classification Search
   CPC ............ A61L 2420/04; A61L 2430/06; A61L 2430/08; A61L 2420/06; A61L 2420/08
   See application file for complete search history.

(56) References Cited

U.S. PATENT DOCUMENTS

| | | | |
|---|---|---|---|
| 8,067,054 B2 * | 11/2011 | Weber | A61F 2/915 264/260 |
| 8,105,374 B2 | 1/2012 | Civelli | |
| 8,123,794 B2 | 2/2012 | Flagle et al. | |
| 8,128,689 B2 | 3/2012 | Weber et al. | |
| 8,157,857 B2 | 4/2012 | Case et al. | |
| 9,668,742 B2 * | 6/2017 | Blum | A61B 17/12109 |
| 2005/0154449 A1 * | 7/2005 | Elmaleh | A61F 2/07 623/1.15 |
| 2011/0009954 A1 | 1/2011 | Cho et al. | |
| 2011/0301696 A1 | 12/2011 | Mangiardi | |
| 2014/0081386 A1 | 3/2014 | Haselby et al. | |

OTHER PUBLICATIONS

European Search Report for corresponding EP 15202721, dated May 13, 2016, 6 pages.

\* cited by examiner

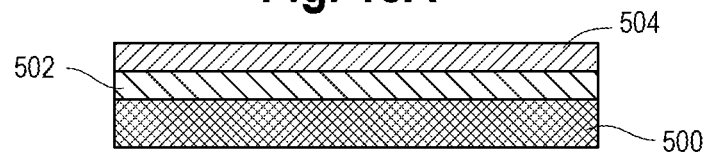
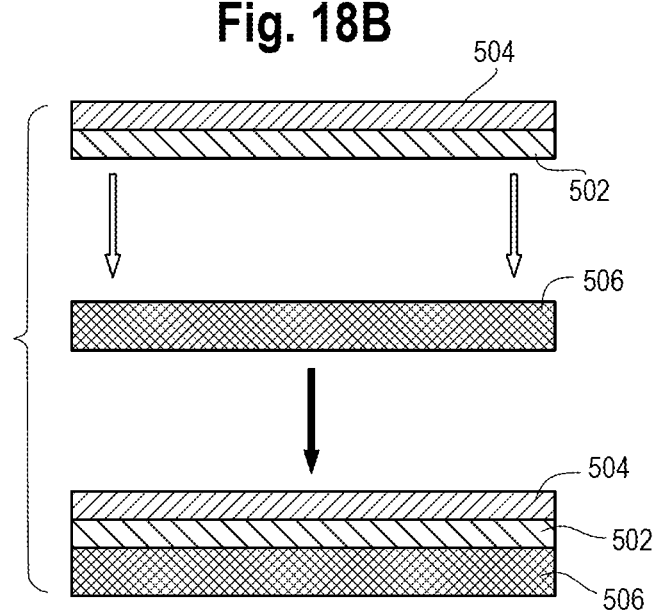
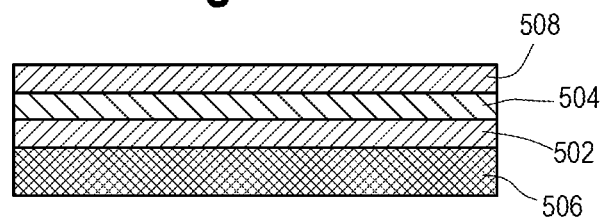

LAYERED MEDICAL DEVICE WITH IMPROVED ADHESION AND METHODS OF MAKING

CROSS-REFERENCE TO RELATED APPLICATIONS

The patent application claims the benefit of the filing date under 35 U.S.C. § 119(e) of U.S. Provisional Patent Application Ser. No. 62/098,871, filed Dec. 31, 2014, which is incorporated herein by reference in its entirety.

TECHNICAL FIELD

This disclosure relates to endoluminal medical devices for implantation within the human or animal body for treatment of endovascular disease. More particularly, it relates to an endoluminal prosthesis having a graft material and methods of manufacturing such an endoluminal prosthesis.

BACKGROUND

Covered stents, or stent grafts, have been used to treat a variety of medical conditions, including aneurysms, occluded vessels, and restenosis. For example, an aneurysm may occur in a blood vessel in a location where, due to age, disease, or genetic predisposition, the blood vessel strength or resiliency is insufficient to enable the blood vessel wall to retain its shape as blood flows therethrough. This may result in ballooning or stretching of the blood vessel at the location having limited strength or resiliency, thereby forming an aneurysmal sac. If the aneurysm is left untreated, the blood vessel wall may continue to expand to the point where the remaining strength of the blood vessel wall is insufficient to prevent rupture. In this instance, the blood vessel may fail at the location of the aneurysm, often with fatal result.

To prevent rupture, a stent graft of a tubular construction may be introduced into the blood vessel, for example, intraluminally. Typically, the stent graft is deployed and secured in a location within the blood vessel such that the stent graft spans the aneurysmal sac. The outer surface of the stent graft, at its opposed ends, may be sealed to the interior wall of the blood vessel at locations where the blood vessel wall has not suffered a loss of strength or resiliency. Blood flow in the vessel may be channeled through the hollow interior of the stent graft, thereby reducing, or possibly eliminating, the stress on the blood vessel wall at the location of the aneurysmal sac. The graft material of the stent graft may be substantially non-porous so that blood may be prevented from leaking into the aneurysmal sac. This may reduce the risk of rupture of the blood vessel wall at the location of the aneurysmal sac while allowing blood to continue to flow through the stent graft to the downstream blood vessels without interruption.

Various materials and methods have been used to create coverings, or grafts, that may be applied to stents to form stent grafts. For example, grafts may be made using woven techniques, thin-sheet/tubing bonding, or other processes. These grafts often require manufacturing efforts and/or post-processing techniques (e.g., gluing, sewing, taping, etc.) to create a covering. Electrospinning may be used to apply a suitable biocompatible coating or covering to a medical device, such as a stent graft. Electrospinning is a process for creating a nonwoven network of fibers using an electrically charged solution that is driven from a source to a target with an electrical field. More specifically, a solution is driven from an orifice, such as a needle. A voltage is applied to the orifice resulting in a charged solution jet or stream from the orifice to the target. The jet forms a conical shape, termed a Taylor cone, as it travels from the orifice. As the distance from the orifice increases, the cone becomes stretched until the jet splits or splays into many fibers prior to reaching the target. The fibers are extremely thin, typically in the nanometer range. The collection of fibers on the target forms a thin mesh layer of fibrous material.

One previous disclosure describes an endoluminal prosthesis for placement within a body vessel may include a tubular support structure. The support structure may include a proximal end segment, a distal end segment, an intermediate segment positioned between the proximal end segment and the distal end segment, a lumen extending longitudinally within the support structure, a luminal surface, and an abluminal surface opposite the luminal surface. The prosthesis may include a first layer of nonwoven electrospun fibers positioned on the luminal surface of the support structure. The prosthesis may include a second layer of nonwoven electrospun fibers positioned on the abluminal surface of the support structure. The support structure may be entirely or partially encapsulated by the above method as shown and described in U.S. Publication No. 2004/0081386 to Haselby et al. and assigned to Cook Medical Technologies, Inc., and incorporated by reference in its entirety.

SUMMARY

The present embodiments provide medical devices, such as endoluminal prostheses having a graft material and methods of manufacturing such medical devices. In particular, the present disclosure provides devices and that have greater adhesion forces between its layers and greater integrity.

In one example, an endoluminal prosthesis for placement within a body vessel may include a tubular support structure. The tubular support structure includes a proximal end segment, a distal end segment, a lumen extending longitudinally within the support structure, a luminal surface, and an abluminal surface opposite the luminal surface. The prosthesis further includes a first sol-gel layer disposed partially or entirely on its luminal surface, a first non-woven layer of fibers disposed over the first sol-gel layer, and a second non-woven layer of fibers disposed over the abluminal surface of the tubular support structure to create a partially or fully encapsulated support structure.

In another example, an endoluminal prosthesis for placement within a body vessel may include a tubular support structure. The support structure may include a proximal end segment, a distal end segment, a lumen extending longitudinally within the support structure, a luminal surface, and an abluminal surface opposite the luminal surface. In this example, the prosthesis includes include a first sol-gel layer disposed partially or entirely on its luminal surface and abluminal surfaces, a first fiber layer disposed over the sol-gel layer on the luminal surface, and a second fiber layer disposed on the sol-gel layer on the abluminal surface of the support structure. In each of the above examples, the above fibers are polymeric fibers, and most preferably are nanofibers or microfibers. Suitable fibers include Polyethylene Terephthalate (PET), polytetrafluoroethylene (PTFE), expanded polytetrafluoroethylene (ePTFE). Most preferably, the polymeric fibers are PET fibers, and most preferably microfibers and/or nanofibers.

In another example, a method is provided for making an endoluminal prosthesis including the steps of depositing fibers, for example by electrospinning a PET solution, onto a rotating mandrel, applying a sol-gel layer, such as $TiO_2$/

SiO₂ sol-gel of varying ratios, to the PET layer, placing the support structure over the PET/sol-gel layer, depositing/electrospinning a second PET solution over the support structure, and removing the encapsulated structure from the mandrel. A further iteration of this method includes first soaking/dipping the support structure in an SiO₂ sol-gel and allowing the sol-gel to dry, depositing/electrospinning PET fibers onto a collection mandrel, applying a sol-gel layer, such as TiO₂/SiO₂ sol-gel of varying ratios, to the PET layer, placing the support structure over the PET/sol-gel layer, depositing/electrospinning a second PET solution over the support structure, and removing the encapsulated structure from the mandrel. In each of the above methods, the support structure may be dried following removal from the mandrel.

In another exemplary method, an electrospun PET covering is created using sheet bonding from either roll-to-roll or flat plate fiber matrix and used to create a stent-graft or covered stent or other medical device. In an exemplary method, a desired thickness of fibers, such as PET, is electrospun onto a collection apparatus to produce sheets of electrospun PET. A TiO₂/SiO₂ sol-gel of varying ratios is applied, for example by spraying, dipping or the like, onto at least one side of the fiber sheet. A tubular structure, such as a stent, which may have been pre-soaked in a SiO₂ sol-gel and allowed to dry may be provided and a sheet of the fiber/sol-gel may be placed on either the luminal surface of the tubular structure, the abluminal surface of the tubular structure or both. Alternatively, a sheet of the material may be wrapped onto a mandrel, the tubular structure placed over the sheet, and a second sheet placed over the tubular structure to partially or entirely encapsulate the tubular structure. One or more sheets may be used on either or both surfaces. The use of sheets permits a covering method that can conform to a number of geometries of medical devices that are not tubular or cylindrical in nature.

The apparatus and methods of the present invention provide a device that has greater adhesion forces between multiple electrospun layers (such as between a PET luminal layer and a PET abluminal layer), that has greater adhesion forces between the PET layer and a metallic or polymeric stent, that has improved covering integrity to withstand compression, delivery and deployment forces from a delivery catheter, and permits a device that may have varying thicknesses along the length of the device based on the layer lamination location.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIGS. 18A, 18B, and 18C illustrate an example of electrospun PET covering created using sheet bonding.

Figure 19A:
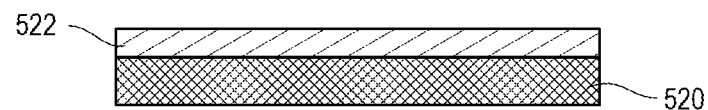
Figure 19B:
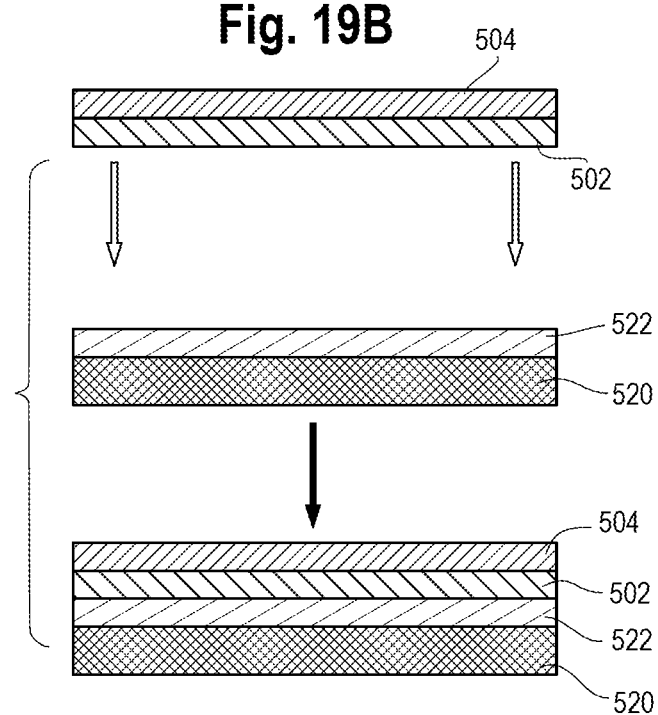
Figure 19C:
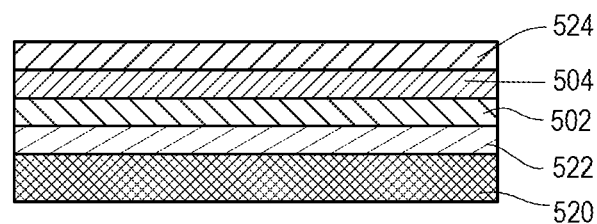

FIGS. 19A, 19B, and 19C illustrate another example of electrospun PET covering created using sheet bonding.

DETAILED DESCRIPTION OF THE DRAWINGS AND THE PRESENTLY PREFERRED EMBODIMENTS

The present disclosure relates to an endoluminal prosthesis having a graft material and methods of manufacturing such an endoluminal prosthesis. An electrospinning process that may be used with the present disclosure is described with regard to FIGS. 1-10 below.

In the present disclosure, the term "proximal" refers to a direction that is generally closest to the heart during a medical procedure, while the term "distal" refers to a direction that is farthest from the heart during a medical procedure.

Figure 1:
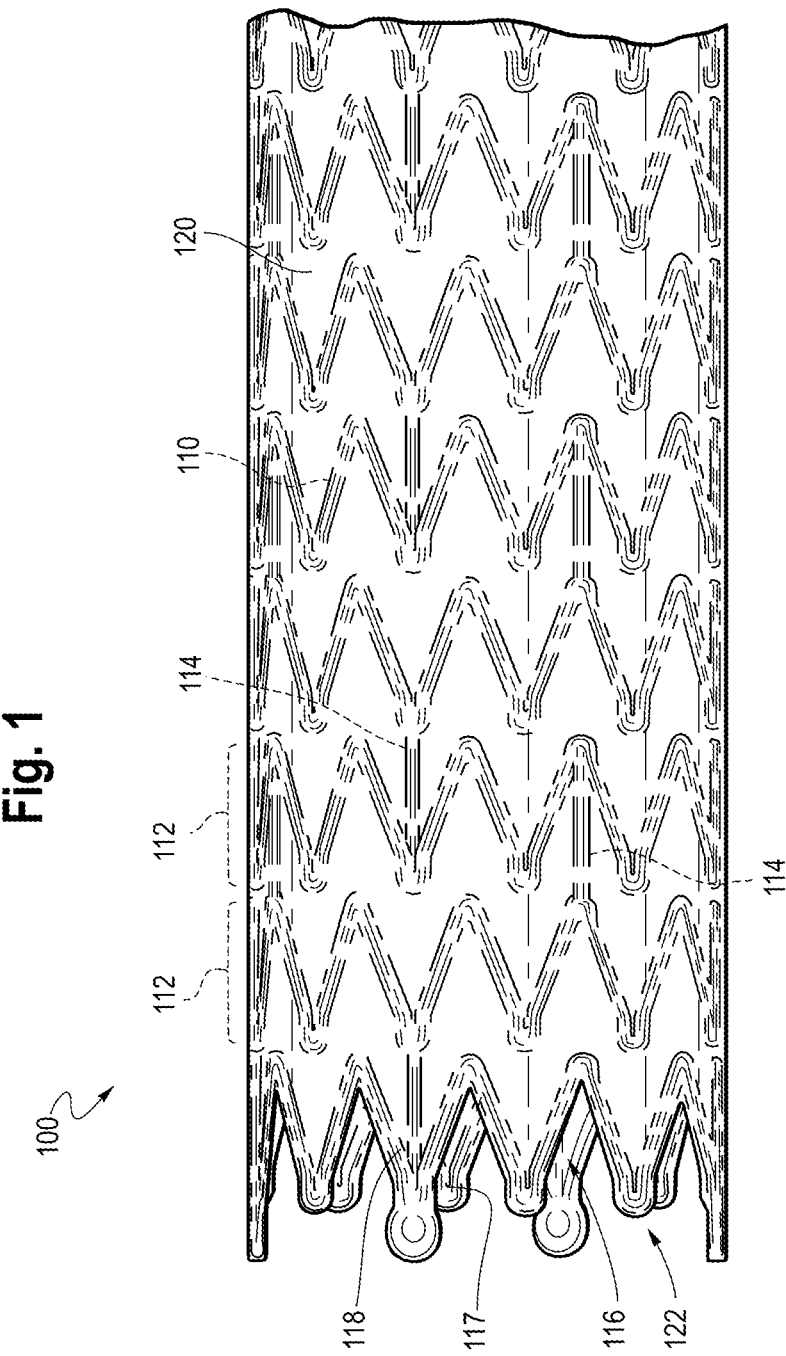
FIG. 1 illustrates one example of an endoluminal prosthesis.

FIG. 1 illustrates one example of an endoluminal prosthesis 100. In this example, the prosthesis 100 is a covered stent or a stent graft. The prosthesis 100 may include a support structure 110 (e.g., a stent) and a graft body 120 attached to the support structure. In one example, the support structure 110 may be partially encapsulated within the graft body 120 as shown in FIG. 1 and further described below. The support structure may have any configuration known in the art. For example, suitable support structures may include any of those described in U.S. Pat. No. 8,123,794 to Flagle et al. and U.S. Pat. No. 8,157,857 to Case et al., both of which are incorporated herein by reference. The support structure may be configured as a unitary structure or a plurality of separate structures which may collectively define the support structure. Additionally, or alternatively, the support structure may be made from a woven wire structure, a laser-cut cannula, individual interconnected rings, or another pattern or design.

In one example, the support structure 110 may include a plurality of ring structures 112 interconnected by connector segments 114 as shown in FIG. 1. Each ring structure 112 may be a ring having an endless undulating pattern (e.g., a zig-zag pattern). The ring structure 112 may be formed by bending a wire into the desired pattern and joining the ends of the wire, by cutting the desired pattern from a solid tube of material, or by any other suitable method. The support structure 110 may be configured as a tubular member defined by the plurality of ring structures 112. For example, the ring structures 112 may be spaced from one another longitudinally along a length of the support structure. The connector segments 114 may extend longitudinally between adjacent ring structures 112 to maintain the spacing between the ring structures.

In one example, the support structure 110 may have a substantially cylindrical shape as shown in FIG. 1. In other words, a transverse cross section of the support structure 110 may have a substantially circular shape. In other examples, the support structure 120 may have any other cross sectional shape including, for example, triangular, rectangular, elliptical, or any other polygonal or non-polygonal shape. A lumen 116 may extend longitudinally within the support structure 110. An inner surface or luminal surface 117 of the support structure 110 may face the lumen 116. In other words, the lumen 116 may be defined by the luminal surface 117 of the support structure 110. The support structure 110 may include an outer surface or abluminal surface 118 positioned opposite the luminal surface 117. In other words, the luminal surface 117 may be positioned inside the support structure, and the abluminal surface 118 may be positioned outside the support structure opposite the luminal surface.

The support structure 110 may add rigidity, expansion force, and/or support to the prosthesis 100. To that end, the support structure 110 may be made from one or more of numerous metals and/or alloys. For example, the support structure 110 may be made from a metallic material such as stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, such as a molybdenum alloy including about 0.4% to about 0.8% of lanthanum oxide ($La_2O_3$), and a nickel-titanium alloy, such as nitinol, or other suitable materials known in the art. In one example, the support structure 110 may include a shape-memory or superelastic material such as nitinol. Use of a shape-memory or superelastic material may enable the support structure 110 to be over-expanded as further described below.

The graft body 120 may be attached to the support structure 110. The graft body 120 may be disposed on the luminal surface 117 and/or the abluminal surface 118 of the support structure 110. In one example, the graft body 120 may be disposed on both the luminal surface 117 and the abluminal surface to encapsulate the support structure 110, or a portion thereof, within the graft body as further described below. The graft body 120 may be configured as a tubular body having any suitable shape as described above with reference to the support structure 110. A lumen 122 may extend longitudinally within the graft body 120. The lumen 122 may be at least partially coextensive with the lumen 116 of the support structure 110. The lumen 122 may be configured to permit blood or other body fluids to flow through the prosthesis within the lumen 122.

As disclosed here, e example, the graft material may be deposited onto the support structure 110 (e.g., the luminal surface 117 and/or the abluminal surface 118) using an electrospinning process as further described below. In other examples, the graft material may be deposited onto the support structure 110 using any other suitable method including, for example, dip coating, spray coating, and melt-spinning. Many different types of biocompatible materials may be used to form the graft body 120. The biocompatible material may be substantially non-toxic in the in vivo environment of its intended use, and may be substantially unrejected by the patient's physiological system (i.e., may be non-antigenic). Examples of biocompatible materials from which a graft material may be formed include, for example, polyesters, such as polyethylene terephthalate (PET); fluorinated polymers, such as polytetrafluoroethylene (PTFE) and fibers of expanded PTFE (ePTFE), polyvinylidene fluoride (PVDF); polyurethanes; and polyolefins. Additionally, or alternatively, materials suitable for making graft materials may include polyethylene, polypropylene, polyvinyl chloride (PVC), polyaramids, polyacrylonitrile, nylon, silicone, cellulose, a biological scaffold or bioremodelable material (e.g., small intestine submucosa (SIS), commercially available from Cook Medical Incorporated, Bloomington, Ind.), or biodegradable materials (e.g., polylactides).

Although the discussion in this disclosure will refer to the prosthesis 100, a person having ordinary skill in the art will recognize that the devices and methods described herein may be equally applicable to a prosthesis, such as a stent or stent graft, having any other configuration. For example, the prosthesis may be configured as a bifurcated stent graft, a stent graft having branches, scallops and/or fenestrations, or a prosthesis having any other shape or features. Such devices and methods are contemplated by and within the scope of this disclosure.

Figure 2:
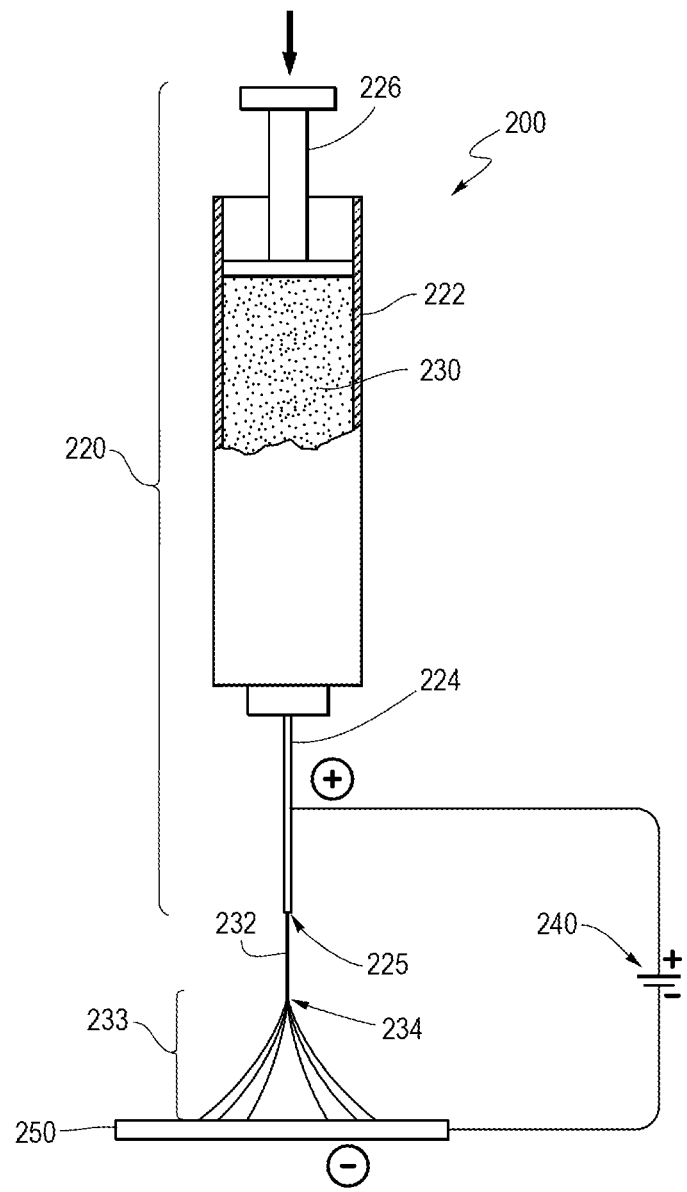
FIG. 2 illustrates one example of an electrospinning apparatus.

FIG. 2 illustrates one example of an electrospinning apparatus 200 for coating an object, such as a substrate or a medical device. The electrospinning apparatus 200 may be similar to that described in U.S. Pat. No. 7,799,261 to Orr et al., which is incorporated herein by reference. For example, the electrospinning apparatus 200 may include a spinneret 220. The spinneret 220 may include a reservoir 222, which may be configured as a syringe-like container as shown in FIG. 2. The reservoir 222 may be fluidly coupled to an orifice 224 to form the spinneret 220. The orifice 224 may be configured as a needle as shown in FIG. 2.

A solution 230 may be loaded into the reservoir 222. Suitable solutions will be discussed in more detail below. The orifice 224 may have a distal opening 225 through which the solution 230 may be driven by a displacement system 226. The displacement system 226 may be configured as any type of controllable, variable rate fluid displacement system. For example, the fluid displacement system 226 may be configured as a plunger as shown in FIG. 2. Preferably, the displacement system 226 may be an automated system to provide a consistent and accurate flow of solution 230 through the orifice 224. In one example, the fluid displacement system 226 may deliver the solution 230 at a delivery rate of about 0 mL/hr to about 25 mL/hr, about 1 mL/hr to about 10 mL/hr, or about 3 mL/hr to about 7 mL/hr.

A voltage source 240 may apply an electric potential across the spinneret 220 and a target 250. In one example, the electric potential may be between about 10 kV and about 35 kV, between about 15 kV and about 30 kV, or between about 20 kV and about 25 kV. The electric potential 240 may aid the displacement system 226 in ejecting the solution 230 from the distal opening 225 of the orifice 224.

The solution may form a charged jet or stream 232 from the distal opening 225 to the target 250. The solution stream 232 may form a conical shape 233, called a Taylor cone, between the spinneret 220 and the target 250. As the solution stream 232 travels away from the opening 225, the cone 233 may begin to splay or stretch at a position 234 between the spinneret 220 and the target 250. In one example, the distance between the distal opening 225 and the target 250 may be between about 0.1 inches to about 6 inches, between about 0.5 inches to about 4 inches, or between about 1 inch to about 2 inches. Position 234 need not be substantially intermediate the distal opening 225 and the target 250, and may be located at any desired distance between the distal opening and the target. The splaying or stretching action may create a plurality of fibers that may or may not dry upon reaching the target 250, depending on the volatility of the chosen solvent. The fibers may contact the target 250 to form a coating of nonwoven fibers thereon. The coating of nonwoven fibers may be configured as a network of fibers deposited on the target 250 to collectively form a sheet of nonwoven fibers.

In one example, an electrospinning apparatus similar to the electrospinning apparatus 200 may be used to prepare an endoluminal prosthesis such as the prosthesis 100 described above. For example, an electrospinning apparatus may be used to apply a graft material to the support structure 110 to form the graft body 120 as further described below.

Figure 3:
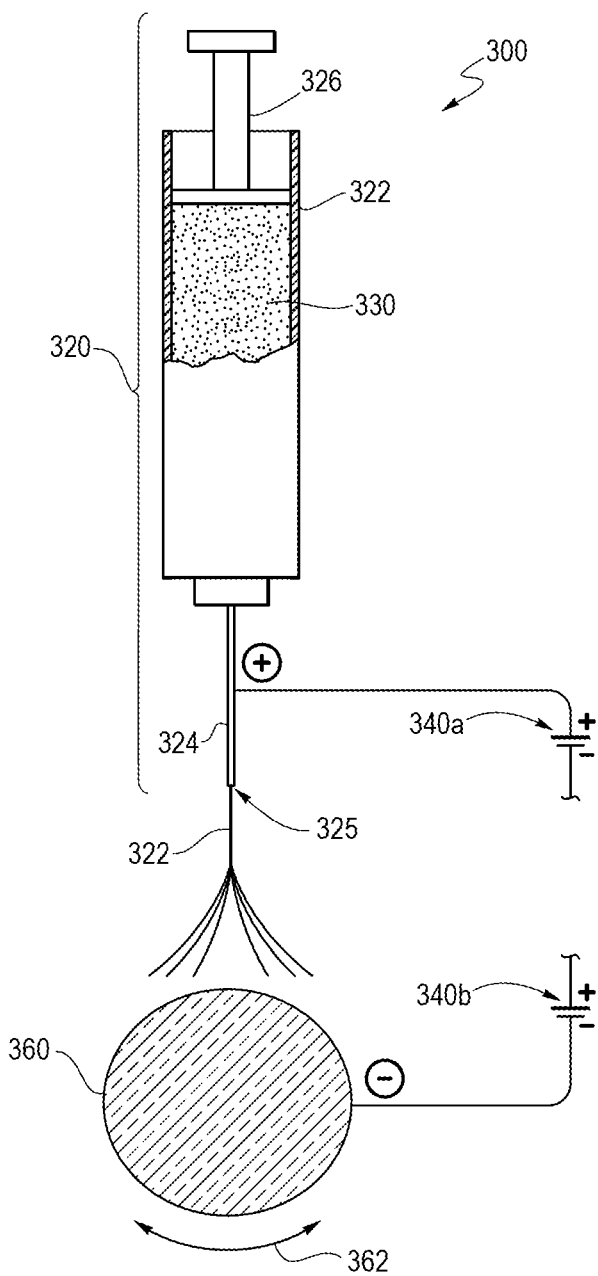
FIG. 3 illustrates an exemplary apparatus and method step for electrospinning a solution onto an outer surface of a mandrel.

FIG. 3 illustrates one example of an electrospinning apparatus 300, which may be used to prepare the endoluminal prosthesis 100 as further described below. For example, the electrospinning apparatus 300 may be used to electrospin a graft material (e.g., PET solution) onto a rotating mandrel to create an encapsulated supporting structure (i.e., stent) within a covering formed by the selected graft material. The electrospinning apparatus 300 may be similar to the electrospinning apparatus 200 described above. For example, the electrospinning apparatus 300 may include a spinneret 320 including a reservoir 322 that is fluidly coupled to an orifice 324. A solution 330 may be loaded into the reservoir 322 and driven by a displacement system 326 through a distal opening 325 of the orifice 324. An electric potential may be applied across the spinneret 320 and a mandrel 360. The solution may form a charged jet or stream 332 from the distal opening 325 to the mandrel 360. As the solution stream 332 travels away from the opening 325, the stream may begin to splay or stretch to create a plurality of fibers. The fibers may contact the mandrel 360 to form a coating of nonwoven fibers thereon.

In one example, a voltage source may apply an electric potential across the spinneret 320 and the mandrel 360 as described above with reference to the voltage source 140. In another example, multiple voltage sources may be used to apply the electric potential. For example, a first voltage source 340a may be electrically coupled to the spinneret 320, and a second voltage source 340b may be electrically coupled to the mandrel 360 as shown in FIG. 3. The first voltage source 340a may generate an electric charge on the orifice 324. In other words, the first voltage source 340a may apply an electric potential between the orifice 324 and ground. Similarly, the second voltage source 340b may generate an electric charge on the mandrel 360. In other words, the second voltage source 340b may apply an electric potential between the mandrel 360 and ground.

The electric charge on the mandrel 360 may have an opposite sign relative to the electric charge on the orifice 324. In one example, the orifice 324 may be positively charged (i.e., the sign of the electric charge may be positive), and the mandrel 360 may be negatively charged (i.e., the sign of the electric charge may be negative). In another example, the orifice 324 may be negatively charged, and the mandrel 360 may be positively charged. The magnitude of the electric charge on the orifice 324 may be the same as or different than the magnitude of the electric charge on the mandrel 360. In one example, the magnitude of the electric charge on the orifice 324 relative to ground may be between about 5 kV and about 20 kV, preferably between about 6 kV and about 7.5 kV. Additionally, or alternatively, the magnitude of the electric charge on the mandrel 360 relative to ground may be between about 5 kV and about 20 kV, preferably between about 6 kV and about 7.5 kV. The orifice 324 and the mandrel 360 may have opposing charges such that the electric potential between the orifice and the mandrel may be between about 10 kV and about 40 kV, preferably between about 12 kV and about 15 kV.

In one example, the spinneret 320 may be configured as a 3 mL plastic syringe (e.g., a NORM-JECT® syringe commercially available from Air-Tite Products Co., Virginia Beach, Va.) equipped with a 23-Gauge disposable polymer-hub stainless steel needle. Additionally, or alternatively, the distance between the orifice 324 and the mandrel 360 may be between about 5 cm and about 25 cm, preferably between about 12 cm and about 15 cm. Additionally, or alternatively, the solution 330 may be extruded using a syringe pump at a substantially constant flow rate between about 0.5 mL/h and about 4 mL/h, preferably between about 0.5 mL/h and about 1.5 mL/h. Additionally, or alternatively, each of the first voltage source 340a and the second voltage source 340b may be configured as a high-voltage power supply capable of applying DC voltage up to about 20 kV.

FIG. 3 illustrates the mandrel 360 in a cross-sectional view taken along a plane transverse to the longitudinal axis of the mandrel. In one example, the mandrel 360 may have a substantially cylindrical shape as shown in FIG. 3. In other examples, the mandrel may have any other suitable shape. Preferably, the mandrel 360 may be sized and shaped for placement within a lumen of a medical device (e.g., the lumen 116 of the support structure 110) as further described below. The mandrel 360 may include an outer surface extending circumferentially and longitudinally along the mandrel.

The mandrel 360 and the spinneret 320 may be movable relative to one another. Such movement may enable the coating of any portion of the outer surface of the mandrel 360. For example, the outer surface may be coated almost entirely, partially, or at discrete locations thereon. For example, the mandrel 360 may be rotatable about the longitudinal axis of the mandrel. In other words, the mandrel 360 may be configured to rotate in a direction indicated by the arrow 362. In one example, the mandrel may be configured to rotate at a speed of between about 80 rpm and about 4000 rpm, or between about 100 rpm and about 500 rpm. The rotational speed of the mandrel 360 may be adjusted to adjust the diameter of the fibers produced during electrospinning. Increasing the rotational speed of the mandrel 360 may reduce the diameter of the fibers. Decreasing the rotational speed of the mandrel 360 may increase the diameter of the fibers. Additionally, or alternatively, the mandrel 360 may be movable in a direction substantially parallel to the longitudinal axis of the mandrel. In other words, the mandrel 360 may be configured to translate (e.g., in a forward or backward longitudinal direction) relative to the spinneret 320. Additionally, or alternatively, the mandrel 360 may be movable in a direction transverse to the longitudinal axis of the mandrel. In other words, the mandrel 360 may be configured to translate (e.g., in an up, down, or sideways transverse direction) relative to the spinneret 320. Such rotation and/or translation (e.g., longitudinal or transverse translation) of the mandrel 360 relative to the spinneret 320 may enable coating of the outer surface of the mandrel, or a portion thereof, with electrospun fibers as further described below. Such a coating may be achieved by any relative motion between the mandrel 360 and the spinneret 320. For example, movement of the mandrel 360 relative to the spinneret 320 may be achieved by maintaining the spinneret in a constant position while moving the mandrel, by maintaining the mandrel in a constant position while moving the spinneret, and/or by moving the mandrel and the spinneret relative to one another. In one example, the mandrel may rotate and the spinneret may translate in a longitudinal direction relative to the mandrel.

The relative movement of the mandrel 360 with respect to the spinneret 320 may influence several properties of the resulting coating of fibers. For example, increasing the speed of the relative motion may cause a reduction in the thickness of the coating. This may be caused, for example, because a portion of the mandrel 360 may be disposed in the path of the stream 332 for a shorter period of time at increased speeds. Additionally, or alternatively, increasing the speed of the relative motion may cause the fibers to be increasingly aligned with one another. This may affect the strength, resiliency, and/or porosity of the coating. Also for example, as the distance between the spinneret 320 and the mandrel 360 is increased, the solution stream 332 may be required to travel a greater distance before reaching the mandrel. This may affect the splaying and/or drying characteristics of the solution stream 332, which may affect the properties of the resultant coating.

In any of the examples described herein, the mandrel 360 may be formed from any suitable conductive material known in the art. For example, the mandrel 360 may be formed from a metallic material such as stainless steel (e.g., electropolished stainless steel) or chrome. In another example, the mandrel 360 may be formed from a non-metallic material such as a conductive plastic material. The mandrel 360 may include a release layer disposed on the outer surface thereof to aid in removing the prosthesis 100 from the mandrel as further described below. The release layer may be formed from any material known in the art. Preferably, the release layer may be formed from a non-stick material such as, for example, PTFE, sodium bicarbonate, a silicone lubricant, or any other biocompatible lubricant.

To prepare the prosthesis 100, a layer of nonwoven fibers may be formed on the outer surface of the mandrel 360 by electrospinning the solution 330 from the orifice 324 onto the outer surface of the mandrel. In one example, the mandrel 360 may be moved rotationally about the longitudinal axis thereof. The solution 330 may be discharged from the orifice 324 and attracted to the mandrel 360 by the electrical potential applied between the orifice and the mandrel as described above. The rotation of the mandrel 360 may cause the resultant coating of nonwoven fibers to be distributed about the circumference of the mandrel. Additionally, or alternatively, the spinneret 320 may be translated longitudinally relative to the mandrel 360 while discharging the solution 330 from the orifice 324. The translation of the spinneret 320 may cause the resultant coating of nonwoven fibers to be distributed about the length of the mandrel. In one example, the mandrel 360 may be rotated and the spinneret 320 may be translated to form a layer of nonwoven fibers covering substantially the entire circumference of the mandrel along at least a portion of the length of the mandrel.

Figure 4:
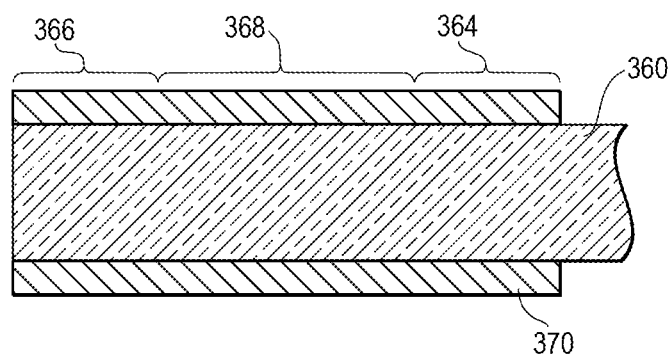
FIG. 4 illustrates one example of a layer of nonwoven electrospun fibers disposed on the outer surface of a mandrel using the method shown in FIG. 3.

FIG. 4 shows a longitudinal cross sectional view of an end portion of the mandrel 360 with a layer 370 of nonwoven electrospun fibers disposed on the outer surface thereof. A working length of the mandrel 360 may include a proximal end segment 364, a distal end segment 366, and an intermediate segment 368 positioned between the proximal end segment and the distal end segment. The mandrel 360 may be rotated and the spinneret 320 may be translated while the solution 330 is electrospun onto the outer surface of the mandrel as described above to distribute the electrospun fibers circumferentially and longitudinally about the outer surface of the mandrel. In one example, the solution 330 may be electrospun onto each of the proximal end segment 364, the distal end segment 366, and the intermediate segment 368 of the mandrel 360 such that the layer 370 may be disposed upon substantially the entire working length of the outer surface of the mandrel as shown in FIG. 4. In other words, each of the proximal end segment 364, the distal end segment 366, and the intermediate segment 368 of the mandrel 360 may be coated with the electrospun fibers. In one example, the spinneret 320 may be programmed to move longitudinally along the length of the mandrel to focus the fibers produced along substantially the entire mandrel length. The spinneret 320 may make any appropriate number of passes along the length of the mandrel 360 to achieve a coating having a desired thickness. In one example, the coating may have a thickness of between about 10 µm and about 70 µm, typically between about 15 µm and about 25 µm, preferably about 20 µm. During each pass, the spinneret 320 may move longitudinally along substantially the entire working length of the mandrel 360. The number of passes may be increased to increase the thickness of the coating of electrospun fibers or decreased to decrease the thickness of the coating of electrospun fibers. In one example, a portion of the mandrel may be uncovered by the layer 370 of nonwoven electrospun fibers to form a partially encapsulated support structure as further described below.

Figure 5:
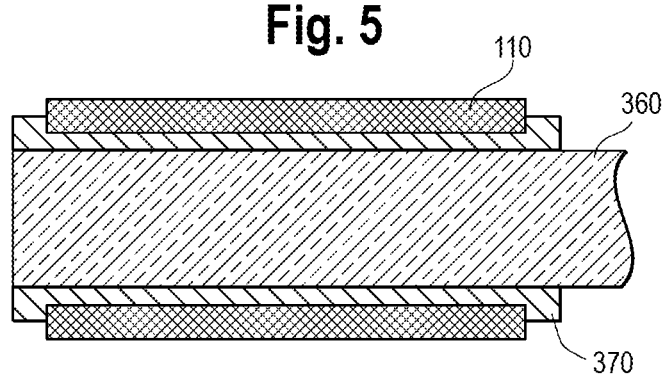
FIG. 5 illustrates one example of a support structure disposed on the layer of nonwoven electrospun fibers of FIG. 4.

The support structure 110 may be placed on the mandrel 360 over the layer 370 of electrospun fibers as shown in FIG. 5. In this manner, the layer 370 of electrospun fibers may be positioned in contact with the luminal surface 117 of the support structure 110. In other words, the layer 370 of nonwoven fibers may be contacted with the luminal surface 117 of the support structure 110 by locating the mandrel at least partially within the lumen 116 of the support structure. In one example, the support structure 110 may have a relaxed diameter. The support structure 110 may be configured to expand to the relaxed diameter after compressing the support structure to a compressed diameter (e.g., for introducing the support structure into a body lumen in a conventional manner) and releasing the support structure in the compressed configuration. Additionally, or alternatively, the support structure 110 may be over-expandable to a diameter that is greater than the relaxed diameter (e.g., by exerting a radially outward force on the support structure in the relaxed diameter). The support structure 110 may contract toward the relaxed diameter upon releasing the support structure in the over-expanded configuration. The support structure 110 may be over-expanded for placement over the mandrel 360. In other words, the support structure 110 may be over-expanded to a first diameter that is greater than the relaxed diameter of the support structure and placed over the mandrel 360. The support structure 110 may be allowed to contract to a second diameter that is smaller than the first diameter to contact the layer 370 of nonwoven fibers on the mandrel 360. The second diameter may be greater than the relaxed diameter of the support structure 110. In other words, the support structure 110 may be over-expanded even in the second diameter configuration.

In one example, the support structure 110 may be embedded in the layer 370 of nonwoven fibers such that the layer extends into one or more openings or interstices of the support structure. In other words, at least a portion of the layer 370 may be positioned within one or more openings (e.g., formed between adjacent ring structures 112 and/or connector segments 114). This may aid in encapsulating the support structure 110 within the graft body 120 as further described below. The over-expanded support structure 110 may produce a radially inward force on the mandrel 360 and/or the layer 370 of nonwoven fibers. In other words, the support structure 110, in the second diameter configuration on the mandrel 360, may squeeze the mandrel and/or the layer 370 of nonwoven fibers. Such an inward force may aid in embedding the support structure 110 within the layer 370 of nonwoven fibers.

Figure 6:
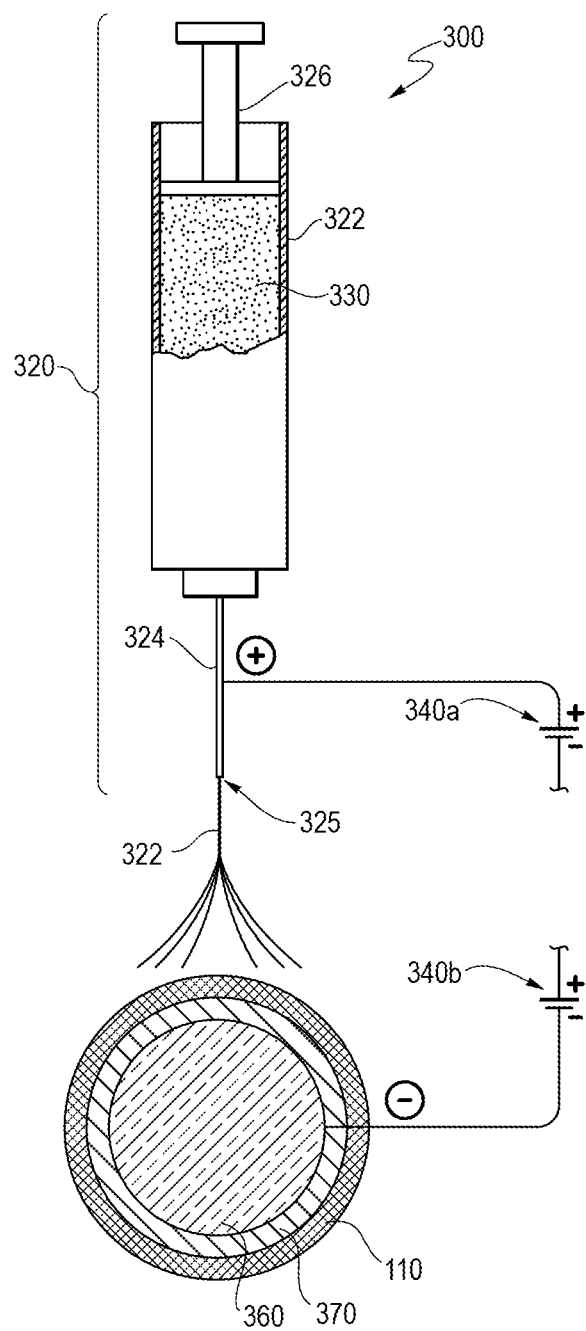
FIG. 6 illustrates an exemplary method step for electrospinning a solution onto an abluminal surface of the support structure of FIG. 5.

A layer of nonwoven fibers may be formed on the abluminal surface 118 of the support structure 110 by electrospinning the solution 330 from the orifice 324 onto the abluminal surface of the support structure. FIG. 6 illustrates the electrospinning apparatus 300 described above configured to form a layer of nonwoven fibers on the abluminal surface 118 of the support structure 110. The support structure 110 may be positioned between the spinneret 320 and the mandrel 360. The solution 330 may be discharged from the spinneret 320 toward the mandrel 360 as described above. The stream 322 may contact the abluminal surface 118 of the support structure 110 to form the layer of nonwoven electrospun fibers on the abluminal surface.

In one example, the mandrel 360 may be moved rotationally about the longitudinal axis thereof, which may cause corresponding rotation of the support structure 110. The solution 330 may be discharged from the orifice 324 and attracted to the mandrel 360 by the electrical potential applied between the orifice and the mandrel as described above. The rotation of the support structure 110 may cause the resultant coating of nonwoven fibers to be distributed about the circumference of the support structure. Additionally, or alternatively, the spinneret 320 may be translated longitudinally relative to the support structure 110 while discharging the solution 330 from the orifice 324. The translation of the spinneret 320 may cause the resultant coating of nonwoven fibers to be distributed about the length of the support structure 110. In one example, the support structure 110 may be rotated and the spinneret 320 may be translated to form a layer of nonwoven fibers covering substantially the entire circumference of the support structure along at least a portion of the length of the support structure.

In one example, the support structure 110 may be electrically charged during electrospinning of the layer of nonwoven fibers on the abluminal surface thereof. In other words, an electrical potential may be applied between the orifice and the support structure 110. The electrical potential may aid in attracting the solution 330 discharged from the orifice 324 as described above. The electrical charge on the support structure 110 may be generated, for example, by the electrical charge on the mandrel 360 and the proximity of the support structure to the mandrel. Additionally, or alternatively, the support structure 110 may be electrically coupled to the mandrel 360 (e.g., with a conductive wire or by contact with the mandrel). The electrical charge on the support structure 110 and/or the mandrel 360 may vary during electrospinning. For example, the electrical charge may be reduced by an insulating effect of the layers of electrospun fibers formed on the mandrel 360 and/or the support structure 110. The electrical charges of the mandrel 360, the support structure 110, and/or the spinneret 320 may be adjusted (e.g., increased) during electrospinning to compensate for such an insulating effect.

Figure 7:
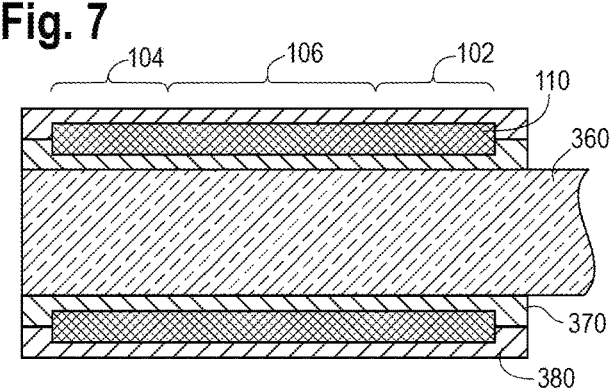
FIG. 7 illustrates the support structure of FIGS. 5-6 disposed between two layers of nonwoven electrospun fibers.

FIG. 7 shows a longitudinal cross sectional view of the support structure 110 positioned on the mandrel 360 between the layer 370 of nonwoven electrospun fibers disposed on the outer surface of the mandrel and a layer 380 of nonwoven electrospun fibers disposed on the abluminal surface 118 of the support structure. The support structure 110 may include a proximal end segment 102, a distal end segment 104, and an intermediate segment 106 positioned between the proximal end segment and the distal end segment. The proximal end segment 102 of the support structure 110 may be positioned adjacent to the proximal end segment 364 of the mandrel 360; the distal end segment 104 of the support structure may be positioned adjacent to the distal end segment 366 of the mandrel; and/or the intermediate segment 106 of the support structure may be positioned adjacent to the intermediate segment 368 of the mandrel. In other words, each segment of the support structure 110 may be at least partially aligned with the corresponding segment of the mandrel 360 as shown in FIG. 7. The support structure 110 may be rotated and the spinneret 320 may be translated while the solution 330 is electrospun onto the abluminal surface 118 of the support structure as described above to distribute the electrospun fibers circumferentially and longitudinally about the abluminal surface of the support structure. In one example, the solution 330 may be electrospun onto each of the proximal end segment 102, the distal end segment 104, and the intermediate segment 106 of the support structure 110 such that the layer 380 may be disposed upon substantially the entire length of the abluminal surface 118 of the support structure as shown in FIG. 7. In other words, each of the proximal end segment 102, the distal end segment 104, and the intermediate segment 106 of the support structure 110 may be coated with the electrospun fibers. Portions of the layer 370 of nonwoven electrospun fibers or the layer 380 of nonwoven electrospun fibers may be omitted during electrospinning or removed from the support structure 110 and/or the mandrel 360 subsequent to electrospinning to form a partially encapsulated support structure as further described below.

Upon forming the layer 380 of electrospun fibers on the abluminal surface 118 of the support structure 110, the support structure may be at least partially encapsulated within a covering formed by the layer 370 of nonwoven fibers and the layer 380 of nonwoven fibers as shown in FIG. 7. In other words, the support structure 110 may be laminated between luminal and abluminal layers of graft material. The layer 370 and the layer 380 may be joined to one another to form the covering around the support structure 110. For example, the layer 370 and the layer 380 may contact one another through the openings formed between the ring structures 112 and the connector segments 114 of the support structure 110. The portions of the layer 370 and the layer 380 in contact with one another may bond to one another to join the layer 370 and the layer 380 to one another. In one example, the support structure 110 may be embedded in the layer 380 of nonwoven fibers as described above with reference to the layer 370 such that the layer 380 and the layer 370 may contact one another through the openings of the support structure. The layer 370 and the layer 380 may be joined to one another during the electrospinning process without an additional bonding process (e.g., heat or pressure bonding) and/or without additional bonding materials (e.g., adhesives, sutures, staples, or clips). The layer 370 and the layer 380 may be disposed on substantially the entire length of the support structure 110 as shown in FIG. 7 to encapsulate substantially the entire support structure between the layer 370 and the layer 380 of electrospun fibers. Portions of the layer 370 or the layer 380 may be omitted or removed to encapsulate a portion of the support structure 110 between the layer 370 and the layer 380 of electrospun fibers while leaving a portion of the support structure unencapsulated as further described below. The covering formed by the layer 370 and the layer 380 of electrospun fibers may form the graft body 120 of the prosthesis 100. The support structure 110 and the covering (i.e., the graft body 120) may collectively form the prosthesis 100 (e.g., a covered stent).

The prosthesis 100 (e.g., the support structure 110 with the layer 370 and the layer 380 of electrospun fibers attached thereto) may be removed from the mandrel 360. To that end, the mandrel 360 may include a release layer applied to the outer surface thereof. The release layer may reduce the attractive force (e.g., adhesive force) or the frictional force between the layer 370 of electrospun fibers disposed on the luminal surface of the support structure 110 and the outer surface of the mandrel 360 to aid in removing the prosthesis 100 from the mandrel in an undamaged condition. Upon removal from the mandrel 360, the support structure 110 may contract to the relaxed diameter. Forming the layer 370 and the layer 380 of electrospun fibers on the support structure 110 in the over-expanded configuration may enhance the flexibility of the prosthesis 100. For example, upon contraction of the support structure 110 to the relaxed diameter, the tension of the layer 370 and/or the layer 380 of electrospun fibers may be reduced, which may enable increased movement or flexibility of the covering.

An excess length of the covering formed by the layer 370 and the layer 380 of electrospun fibers may extend beyond at least one of the proximal end segment or the distal end segment of the support structure 110 as shown in FIG. 7. At least a portion of the excess length of the covering may be removed from the prosthesis 100. In other words, the excess covering material extending beyond one or more of the ends of the support structure 110 may be trimmed from the prosthesis 100 such that the ends of the covering may be substantially aligned with the ends of the support structure.

The thickness of the graft body 120 of the prosthesis 100 may be manipulated by the electrospinning operator (e.g., by adjusting the speed of rotation and/or translation) for desired operational use. Additionally, or alternatively, the fully or partially encapsulated electrospun covered support structure (e.g., the covered stent) may be post-processed using manufacturing techniques (e.g., laser welding/marking, mechanical punching, etc.) to create varying porosity if desired. Additionally, or alternatively, the graft or covering material may be electrospun simultaneously with additional polymers, additives, or pharmacological agents to promote mechanical and/or chemical characteristics of the prosthesis. For example, the graft or covering material may be electrospun simultaneously with additional polymers such as PET (e.g., DACRON®, commercially available from Invista, Wichita, Kans.) or polyurethane (e.g., THORALON®, commercially available from Thoratec, Pleasanton, Calif.). In one example, the graft or covering material may include PET and polyurethane. Additionally, or alternatively, the graft or covering material may be electrospun simultaneously with additives or pharmacological agents such as, for example, lauric acid, levulinic acid, or polyethylene glycol (e.g., having a molecular weight of about 300, about 600, or any other suitable molecular weight). Electrospinning the graft or covering material with other materials may affect the mechanical properties (e.g., flexibility or strength) of the graft or covering material. Additionally, or alternatively, electrospinning the graft or covering material with other materials may affect the frictional properties and/or enable a reduced profile of the graft or covering material.

Figure 8:
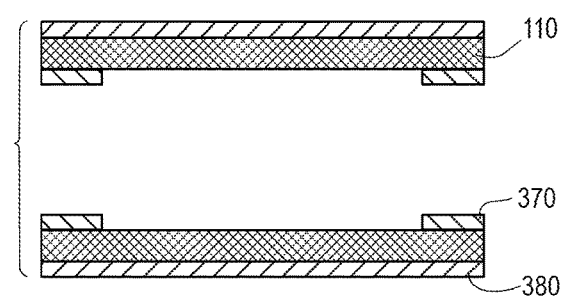
FIG. 8 illustrates one example of a partially encapsulated support structure.

The support structure 110 may be substantially entirely or partially encapsulated within the covering to form the prosthesis 100. In other words, the prosthesis may be configured as a fully or partially encapsulated stent. FIG. 8 illustrates one example of the support structure 110 partially encapsulated within the covering to form a partially encapsulated stent. The layer 370 of nonwoven fibers may be disposed upon only a portion of the length of the luminal surface 117 of the support structure 110. This may be achieved by forming the layer 370 of nonwoven fibers on a portion of the working length of the mandrel 360 during preparation of the prosthesis. In one example, substantially the entire working length of the mandrel 360 may be coated with the layer 370 of nonwoven fibers as described above. A portion of the layer 370 may be selectively removed from the mandrel. For example, a central portion of the layer 370 disposed on the intermediate segment 368 of the mandrel 360 may be removed. The portion of the layer 370 may be removed from the mandrel in any suitable manner such as, for example, severing the layer 370 at the ends of the intermediate segment 368 (e.g., between the intermediate segment and each of the proximal end segment 364 and the distal end segment 366) and lifting the nonwoven fibers from the mandrel.

In another example, the layer 370 may be formed on a portion of the working length of the mandrel 360 by controlling the movement of the spinneret 320 and the mandrel 360 relative to one another during the electrospinning process as described above. For example, the longitudinal translation of the spinneret 320 may be limited such that substantially no fibers are electrospun onto the intermediate segment 368 of the mandrel. Additionally, or alternatively, the flow of the solution 330 from the orifice 325 may be interrupted (e.g., stopped and restarted) during the electrospinning process to avoid electrospinning fibers onto the intermediate segment 368 of the mandrel 360. In other words, a portion of the layer 370 may be electrospun on the proximal end segment 364 of the mandrel 360, and another portion of the layer 370 may be electrospun on the distal end segment 366. The flow of the solution 330 may be interrupted as the spinneret moves across the intermediate segment 368 of the mandrel 360 so that substantially no fibers are electrospun onto the intermediate segment.

In yet another example, the layer 370 may be formed on a portion of the working length of the mandrel 360 by shielding a portion of the mandrel during the electrospinning process. For example, a portion of the mandrel (e.g., the intermediate segment 368) may be covered with a shielding material (e.g., a removable non-adhesive material, such as TEFLON® tubing, or a band of insulating tape) so that the covered portion of the mandrel remains uncoated during the electrospinning process. In still another example, a diffusion template may be used to shield a portion of the mandrel. For example, the diffusion template may be configured as a plate including an opening formed therein. The plate may be placed between the spinneret 320 and the mandrel 360 to obstruct the electrospun fibers from reaching a determined portion (e.g., the intermediate segment 368) of the mandrel.

The support structure 110 may be placed on the mandrel 360 over the layer 370 of nonwoven fibers with the intermediate segment 106 of the support structure substantially aligned with the uncovered intermediate segment 368 of the mandrel. The layer 380 of nonwoven fibers may be formed on the abluminal surface 118 of the support structure as described above. In this manner, a prosthesis having an abluminal covering with luminal end encapsulation at each of the proximal and distal ends may be formed. The proximal end segment 102 and the distal end segment 104 of the support structure 110 may be encapsulated within the covering formed by the layer 370 and the layer 380 of nonwoven electrospun fibers. The graft material covering may be bonded to the support structure 110 by the end encapsulation of the proximal end segment 102 and the distal end segment 104. Such end encapsulation may provide a strong adhesion between the graft material and the support structure at the ends of the prosthesis. The intermediate segment 106 of the luminal surface 117 of the support structure 110 may be uncovered. In other words, the intermediate segment of the support structure may be unencapsulated.

Figure 9:
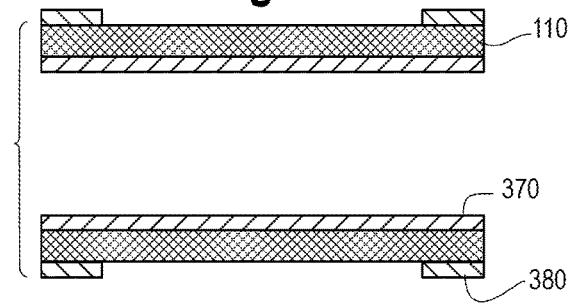
FIG. 9 illustrates another example of a partially encapsulated support structure.

FIG. 9 illustrates another example of the support structure 110 partially encapsulated within the covering to form a partially encapsulated stent. The layer 370 of nonwoven fibers may be disposed upon substantially the entire length of the luminal surface 117 of the support structure 110 by electrospinning the solution 330 onto substantially the entire working length of the mandrel 360 as described above. The layer 380 of nonwoven fibers may be disposed upon only a portion of the length of the support structure 110. In one example, substantially the entire length of the support structure 110 may be coated with the layer 380 of nonwoven fibers as described above. A portion of the layer 380 may be removed from the support structure 110. For example, a central portion of the layer 380 disposed on the intermediate segment 106 of the support structure 110 may be removed. The portion of the layer 380 may be removed from the support structure 110 in any suitable manner as described above with reference to removing a portion of the layer 370 from the mandrel 360. In another example, the layer 380 may be formed on a portion of the length of the support structure 110 by controlling the movement of the spinneret 320 and the mandrel 360 relative to one another during the electrospinning process as described above. For example, the longitudinal translation of the spinneret 320 may be limited and/or the flow of solution 330 may be interrupted such that substantially no fibers are electrospun onto the intermediate segment 106 of the support structure 110. In yet another example, the layer 380 may be formed on a portion of the length of the support structure 110 by shielding a portion of the support structure during the electrospinning process as described above. For example, a portion of the support structure (e.g., the intermediate segment 106) may be covered with a length of removable, non-adhesive material (e.g., TEFLON® tubing) which may keep material off of a portion of the abluminal surface (e.g., the central abluminal surface) so that the covered portion of the support structure remains uncoated during the electrospinning process.

In this manner, a prosthesis having a luminal covering with abluminal end encapsulation at each of the proximal and distal ends may be formed. The proximal end segment 102 and the distal end segment 104 of the support structure 110 may be encapsulated within the covering formed by the layer 370 and the layer 380 of nonwoven electrospun fibers, and the intermediate segment 106 of the abluminal surface 117 of the support structure may be uncovered. In other words, the intermediate segment of the support structure may be unencapsulated.

Figure 10:
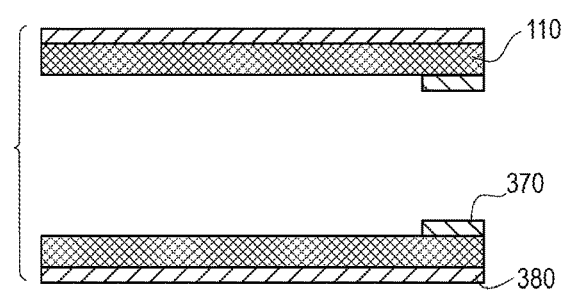
FIG. 10 illustrates another example of a partially encapsulated support structure.

FIG. 10 illustrates another example of the support structure 110 partially encapsulated within the covering to form a partially encapsulated stent. The prosthesis may include an abluminal covering with luminal end encapsulation at only one of the proximal end or the distal end of the prosthesis. This may be achieved by forming the layer 370 on a only a portion of the length of the luminal surface 117 of the support structure 110 as described above and forming the layer 380 on substantially the entire length of the abluminal surface 118 of the support structure also as described above. One of the proximal end segment 102 or the distal end segment 104 of the support structure 110 may be encapsulated within the covering formed by the layer 370 and the layer 380 of nonwoven electrospun fibers, and the other of the proximal end segment 102 or the distal end segment 104 may be uncovered along the luminal surface thereof. The intermediate segment 106 of the luminal surface 117 of the support structure may be uncovered. In other words, one of the proximal end segment or the distal end segment and the intermediate segment of the support structure may be unencapsulated. Although FIG. 10 illustrates a prosthesis including an abluminal covering with proximal end encapsulation, a prosthesis having an abluminal covering with distal end encapsulation or a luminal covering with proximal end encapsulation or distal end encapsulation may be formed in a similar manner.

A covering formed by electrospinning as described herein may include a plurality of nonwoven fibers. In other words, the electrospun fibers may be configured as a mesh of fibers as opposed to a patterned weave or knit of fibers. The electrospun fibers may be nanofibers having a diameter of less than about 1,000 nm. Additionally, or alternatively, the electrospun covering may substantially conform to the underlying support structure. In other words, the electrospun covering may substantially take the shape of the support structure and may be substantially free of ridges or puckering which may be caused by mechanical attachment mechanisms (e.g., sutures). Additionally, or alternatively, the electrospun covering may be substantially seamless. In other words, the covering may be substantially free of seams which may be formed, for example, by stitching together or otherwise attaching adjacent edges of one or more sheets of graft material.

In other examples, a partially encapsulated support structure may be formed using any other suitable method including, for example, dip coating, spray coating, and melt-spinning. For example, a layer of graft material may be deposited on the outer surface of a mandrel by dipping the mandrel into a volume of liquid graft material. The liquid graft material on the outer surface of the mandrel may be dried or cured to form a layer of graft material on the mandrel. A support structure may be placed over the layer of graft material formed on the mandrel, and an end portion of the mandrel and the support structure may be dipped into the volume of liquid graft material to deposit a layer of graft material on the abluminal surface of the support structure. In this manner, the end portion of the support structure may be encapsulated between the two layers of graft material. The opposite end portion of the mandrel and the support structure may be dipped into the volume of liquid graft material to encapsulate the other end portion if desired. A partially encapsulated support structure may be formed in a similar manner using any other suitable method to deposit a layer of graft material on a surface of the mandrel and/or the support structure.

Applying a covering material to a support structure by electrospinning and/or encapsulating only a portion of the support structure as described herein may enable formation of a prosthesis having a reduced profile. For example, the covering may be attached to the support structure without the use of any attachment material (e.g., suture, tape, such as PTFE-FEP bonding tape, glue, or lamination material) or additional processing steps (e.g., mechanical attachment, pressure bonding, chemical treatment, or thermal bonding). In other words, the prosthesis may be substantially free of an extrinsic attachment mechanism. Such attachment material may increase the thickness of the coating resulting in a prosthesis having a larger profile. Additionally, or alternatively, partial encapsulation may provide a prosthesis having a reduced amount of covering material compared to a fully encapsulated support structure, which may result in a reduced profile. In one example, the thickness of a portion of the graft body (e.g., a portion of the covering corresponding or positioned adjacent to the intermediate segment of the support structure) may have a thickness of less than about 70 µm, preferably less than about 25 µm. A graft body with a reduced thickness may enable a prosthesis having a reduced profile. In other words, reducing the thickness of the graft body may enable reduction of the profile (e.g., the thickness or the diameter) of the prosthesis. Such a low-profile prosthesis may be delivered using a sheath having a reduced profile relative to conventional introducer sheaths. This may aid in advancing the sheath within a body vessel to the delivery site within the patient's anatomy.

Partial encapsulation of a support structure may enable a prosthesis having increased flexibility compared to a fully encapsulated support structure. For example, a low-profile prosthesis may have increased flexibility resulting from, for example, lack of attachment materials and/or reduced thickness. Increased flexibility may enable increased maneuverability to deliver the prosthesis through tortuous anatomy. Leaving portions of the support structure uncovered (i.e. partial encapsulation of the support structure) may enable at least a portion of the graft body to slide relative to the support structure. For example, as the prosthesis is compressed (e.g., to be loaded into a delivery device), the length of the support structure may increase. One end of the graft body may be unattached to the support structure. The support structure may be capable of moving relative to the unattached portion of the graft body. For example, the unattached portion of the graft body may be capable of sliding relative to the support structure so that the length of the support structure relative to the graft body may change. In one example, the length of the graft body may remain substantially constant as the length of the support structure changes. This may reduce the potential for stretching or damaging (e.g., by ripping or tearing) the graft material during contraction and/or expansion of the prosthesis.

Direct encapsulation of the support structure may reduce abrasive forces between the graft material and the support structure. For example, the portion of the support structure encapsulated within the graft material may be substantially unable to move relative to the graft material, thereby reducing abrasion between the encapsulated support structure and the graft material. Additionally, or alternatively, direct encapsulation of the support structure may enable formation of a substantially non-porous graft material that is substantially free of suture holes or other openings formed therein.

Solutions for use in the electrospinning process of the present disclosure may include any suitable liquids containing materials to be electrospun (e.g., any of the graft materials described above). For example, solutions may include, but are not limited to, suspensions, emulsions, melts, and hydrated gels containing the materials, substances, or compounds to be electrospun. Solutions also may include solvents or other liquids or carrier molecules. Solutions may include, for example, any of the materials described in U.S. Pat. No. 7,799,261 to Orr et al., which is incorporated herein by reference. In one example, the solution 330 may include a PET such as, for example a DACRON® leg-fabric commercially available from Invista, Wichita, Kans. The solution 330 may include a polymer solution of PET in approximately 50:50 trifluoroacetic acid (TFA) and dichloromethane (DCM or methylene chloride) at a predetermined concentration, typically between about 0.10 g/mL and about 0.17 g/mL solvent.

Additionally, or alternatively, solutions may include one or more bioactive agents. A therapeutically effective amount of a bioactive agent may be incorporated into the graft material produced by the electrospinning process for implantation within a patient. The bioactive agent may be selected to perform a desired function upon implantation. For example, the bioactive agent may be selected to treat indications such as atherosclerosis, renal dialysis fistulae stenosis, or vascular graft stenosis. A graft material including a bioactive agent may be useful when performing procedures such as coronary artery angioplasty, renal artery angioplasty, or carotid artery surgery. Also for example, a bioactive agent such as a growth factor may be selected to promote ingrowth of tissue from the interior wall of a body vessel. An anti-angiogenic or antineoplastic bioactive agent such as paclitaxel, sirolimus, or a rapamycin analog, or a metalloproteinase inhibitor such as batimastaat may be included to mitigate or prevent undesired conditions in the vessel wall, such as restenosis. Many other types of bioactive agents also may be included in the solution.

Although the electrospinning process has been described in relation to applying a graft material covering to a support structure, this disclosure is not so limited. The electrospinning process described above may be used to apply any type of coating to any type of medical device. For example, the electrospinning process may be used to apply a coating of a therapeutic agent to a stent or a covered stent (e.g., a stent graft).

In one example, a method for preparing an endoluminal prosthesis may include providing a support structure including a proximal end segment, a distal end segment, a lumen extending longitudinally within the support structure, a luminal surface, and an abluminal surface opposite the luminal surface. The method may include providing an electrospinning apparatus including an orifice and a mandrel. An electric potential may be applied between the orifice and the mandrel. A first layer of nonwoven fibers may be formed on an outer surface of the mandrel by electrospinning a solution from the orifice onto the outer surface of the mandrel. The first layer of nonwoven fibers may be contacted with the luminal surface of the support structure by locating the mandrel at least partially within the lumen of the support structure. A second layer of nonwoven fibers may be formed on the abluminal surface of the support structure by electrospinning the solution from the orifice onto the abluminal surface of the support structure. The support structure may be partially encapsulated within a covering formed by the first layer of nonwoven fibers and the second layer of nonwoven fibers so that at least a portion of the support structure is unencapsulated within the covering.

An excess length of the covering may extend beyond at least one of the proximal end segment or the distal end segment of the support structure, and the method may include trimming at least a portion of the excess length of the covering from the partially encapsulated support structure. A first electrical charge may be applied to the orifice, and a second electrical charge may be applied to the mandrel. The second electrical charge may be opposite of the first electrical charge. Electrospinning the solution from the orifice onto the outer surface of the mandrel may include electrospinning a first solution from the orifice onto the outer surface of the mandrel, electrospinning the solution from the orifice onto the abluminal surface of the support structure may include electrospinning a second solution from the orifice onto the abluminal surface of the support structure, and the first solution may be different from the second solution.

The support structure may include an intermediate segment positioned between the proximal end segment and the distal end segment of the support structure, and the outer surface of the mandrel may include a first end segment corresponding to the proximal end segment of the support structure, a second end segment corresponding to the distal end segment of the support structure, and an intermediate segment corresponding to the intermediate segment of the support structure. The first layer of nonwoven fibers may cover at least one of the first end segment or the second end segment of the outer surface of the mandrel, the intermediate segment of the outer surface of the mandrel may be substantially uncovered by the first layer of nonwoven fibers, and the second layer of nonwoven fibers may cover each of the proximal end segment, the distal end segment, and the intermediate segment of the abluminal surface of the support structure. At least one of the proximal end segment or the distal end segment of the support structure corresponding to the at least one of the first end segment or the second end segment of the outer surface of the mandrel may be encapsulated within the covering formed by the first layer of nonwoven fibers and the second layer of nonwoven fibers, and the intermediate segment may be unencapsulated within the covering. Forming the first layer of nonwoven fibers on the outer surface of the mandrel may include electrospinning the solution from the orifice onto the intermediate segment of the outer surface of the mandrel and uncovering the intermediate segment of the outer surface of the mandrel by removing a central portion of the first layer of nonwoven fibers disposed on the intermediate segment of the outer surface of the mandrel. The first layer of nonwoven fibers may cover each of the first end segment, the second end segment, and the intermediate segment of the outer surface of the mandrel, the second layer of nonwoven fibers may cover at least one of the proximal end segment or the distal end segment of the abluminal surface of the support structure, and the intermediate segment of the abluminal surface of the support structure may be substantially uncovered by the second layer of nonwoven fibers. The at least one of the proximal end segment or the distal end segment of the support structure may be encapsulated within the covering formed by the first layer of nonwoven fibers and the second layer of nonwoven fibers, and the intermediate segment may be unencapsulated within the covering.

Contacting the first layer of nonwoven fibers with the luminal surface of the support structure may include over-expanding the support structure to a first over-expanded diameter, and allowing the support structure to contract to a second over-expanded diameter over the first layer of nonwoven fibers. The first over-expanded diameter may be larger than the second over-expanded diameter, and the second over-expanded diameter may be larger than a relaxed diameter of the support structure.

In one example, a method for preparing an endoluminal prosthesis may include providing a support structure including a first end segment, a second end segment, an intermediate segment positioned between the first end segment and the second end segment of the support structure, a lumen extending longitudinally within the support structure, a luminal surface, and an abluminal surface opposite the luminal surface. The method may include providing an electrospinning apparatus including an orifice and a mandrel. The mandrel may include a first end segment, a second end segment, and an intermediate segment positioned between the first end segment and the second end segment of the mandrel. A first electrical charge may be applied to the orifice. A second electrical charge may be applied to the mandrel. A first layer of nonwoven fibers may be formed on an outer surface of the mandrel by electrospinning a solution from the orifice onto the first end segment of the mandrel. The mandrel may be located at least partially within the lumen of the support structure. The first end segment of the support structure may be aligned with the first end segment of the mandrel, the second end segment of the support structure may be aligned with the second end segment of the mandrel, and the intermediate segment of the support structure may be aligned with the intermediate segment of the mandrel. The first layer of nonwoven fibers may be contacted with the luminal surface of the support structure. The first layer of nonwoven fibers may cover the luminal surface of the first end segment of the support structure. A second layer of nonwoven fibers may be formed on the abluminal surface of the support structure by electrospinning the solution from the orifice onto the abluminal surface of the first end segment of the support structure. The second layer of nonwoven fibers may cover the abluminal surface of the first end segment of the support structure. The first end segment of the support structure may be encapsulated within a covering formed by the first layer of nonwoven fibers and the second layer of nonwoven fibers. One of the luminal surface or the abluminal surface of at least one of the intermediate segment or the second end segment of the support structure may be uncovered by the respective first layer of nonwoven fibers or second layer of nonwoven fibers.

Forming a first layer of nonwoven fibers on an outer surface of the mandrel may include electrospinning the solution from the orifice onto the second end segment of the mandrel. The first layer of nonwoven fibers may cover the luminal surface of the second end segment of the support structure. Forming a second layer of nonwoven fibers on the abluminal surface of the support structure may include electrospinning the solution from the orifice onto the abluminal surface of the second end segment of the support structure. The second layer of nonwoven fibers may cover the abluminal surface of the second end segment of the support structure. Both the first end segment and the second end segment of the support structure may be encapsulated within the covering formed by the first layer of nonwoven fibers and the second layer of nonwoven fibers.

Forming a first layer of nonwoven fibers on an outer surface of the mandrel may include electrospinning the solution from the orifice onto the intermediate segment of the mandrel. The first layer of nonwoven fibers may cover the luminal surface of the intermediate segment of the support structure. The abluminal surface of the intermediate segment of the support structure may be uncovered by the second layer of nonwoven fibers. The intermediate segment of the support structure may be unencapsulated within the covering formed by the first layer of nonwoven fibers and the second layer of nonwoven fibers.

The luminal surface of the intermediate segment of the support structure may be uncovered by the first layer of nonwoven fibers. Forming a second layer of nonwoven fibers on the abluminal surface of the support structure may include electrospinning the solution from the orifice onto the abluminal surface of the intermediate segment of the support structure. The second layer of nonwoven fibers may cover the abluminal surface of the intermediate segment of the support structure. The intermediate segment of the support structure may be unencapsulated within the covering formed by the first layer of nonwoven fibers and the second layer of nonwoven fibers.

Forming a first layer of nonwoven fibers on an outer surface of the mandrel may include electrospinning the solution from the orifice onto each of the first end segment, the second end segment, and the intermediate segment of the mandrel, and selectively removing a portion of the nonwoven electrospun fibers from at least one of the second end segment or the intermediate segment of the mandrel.

Referring to FIGS. 11-18, the present medical devices and methods for making them are described in further detail and with reference to the prophetic examples provided below.

Figure 11:
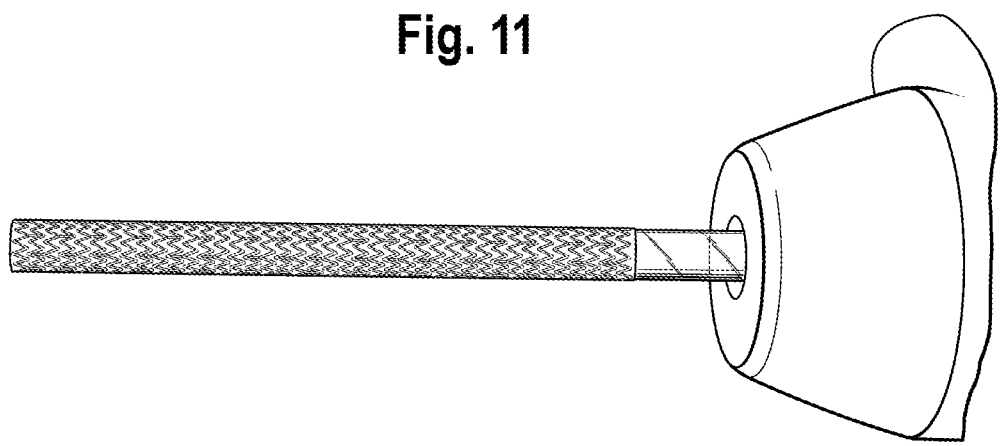
FIG. 11 illustrates an example of a covered support structure on a cylindrical mandrel.

FIG. 11 shows an example of a covered support structure, such as a stent, on a collection surface, such as a cylindrical mandrel. The collection surface may be sized and shaped to correspond to a desired size and shape of a graft material for covering a support surface such as a stent graft. The collection surface can be made of any material which is conductive. The material of the collection surface may be selected from stainless steel, copper, cobalt chrome, nickel titanium (e.g. nitinol), chrome-plated steel, magnesium alloys, and combinations thereof.

Figure 12:
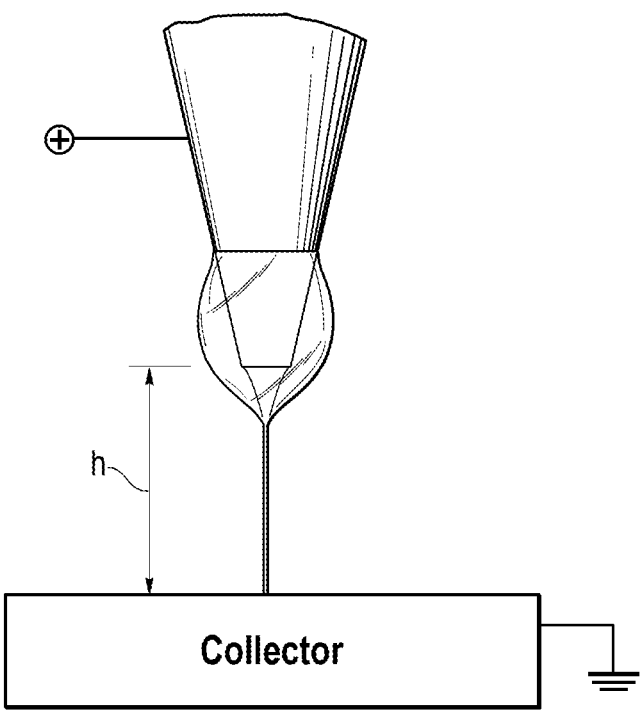
FIG. 12 illustrates an example of electrospinning apparatus and a cylindrical mandrel.

FIG. 12 shows an example of an electrospinning apparatus. Here, for example, PET fibers are spun onto a rotating cylindrical mandrel. Specifically, a PET-polymer solution is driven from the probe tip of FIG. 12. A voltage is applied to the orifice resulting in a charged solution jet or stream from the orifice to the collector surface of the mandrel. The jet forms a conical shape, termed a Taylor cone, as it travels from the orifice. As the distance from the orifice increases, the cone becomes stretched until the jet splits or splays into many PET fibers prior to reaching the collector surface. The PET fibers are extremely thin, typically in the nanometer range. The collection of PET fibers on the mandrel forms a thin mesh layer of fibrous material. In one example, the layer may have a thickness of between about 10 µm and about 70 µm, typically between about 15 µm and about 25 µm, preferably about 20 µm. The number of passes may be increased to increase the thickness of the coating of electrospun fibers or decreased to decrease the thickness of the coating of electrospun fibers. In one example, a portion of the mandrel may be uncovered by the nonwoven layer of fibers to form a partially encapsulated support structure as further described below.

Figure 13A:
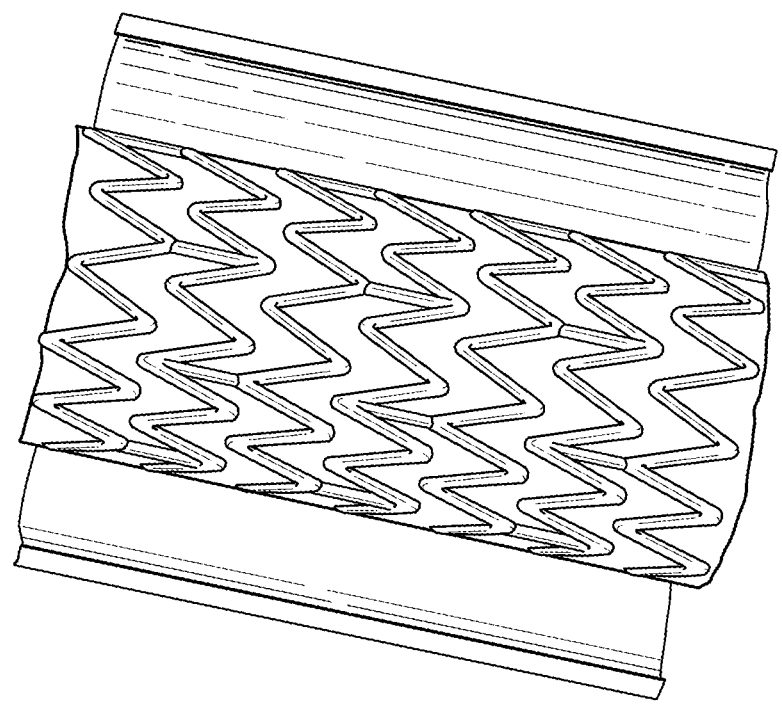
FIG. 13A illustrates an example of a covered stent.

FIG. 13A shows another example of a covered medical device. The medical device includes a support structure having a proximal end, a distal end, a lumen extending longitudinally through the support structure, a luminal (inner) surface, and an abluminal (outer) surface opposite the luminal surface. The support structure may comprise a stent of interconnected components or may be a stent of discrete spaced interconnected components such as rings of varying configurations, including zig zag rings. The stent may be metallic or polymeric. For example, the stent may be stainless steel, nitinol, or any other known suitable stent material that is now known or many become known. In this example, the stent is nitinol.

The medical device includes a first non-woven layer of fibers disposed at least partially over the luminal surface of the support structure. In other words, the layer of fibers partially or fully covers the support structure, including any interstices between stent components. The first non-woven layer of fibers may cover the majority of the luminal surface of the support structure. In yet another example, the support structure includes a first non-woven layer of fibers covering the entire luminal surface of the support structure. In yet other examples, only the internal ends of the support structure are covered by the fiber layer or only an internal intermediate section of the support structure is covered. In yet another example, bands of the fiber layer may be disposed on the interior surface and may be circumferential or longitudinal.

The first non-woven layer of fibers includes polymeric fibers and may consist essentially of polymeric fibers. However, other components such as elutable materials such as therapeutic materials may be included in the polymer fiber solution used to create the fiber layer, so long as the structural integrity of the ultimate fiber layers is not substantially comprised.

In one example, a solution for electrospinning may further comprise bioactive materials, for example a therapeutically effective amount of one or more bioactive agents in pure form or in derivative form. Preferably, the derivative form is a pharmaceutically acceptable salt, ester or prodrug form. Alternatively, a medical device may be implanted in combination with the administration of a bioactive agent from a catheter positioned within the body near the medical device, before, during or after implantation of the device.

Bioactive agents that may be used include, but are not limited to, pharmaceutically acceptable compositions containing any of the bioactive agents or classes of bioactive agents listed herein, as well as any salts and/or pharmaceutically acceptable formulations thereof.

The bioactive agent may be coated on any suitable part of the medical device. Selection of the type of bioactive agent and the portions of the medical device comprising the bioactive agent may be chosen to perform a desired function upon implantation. For example, the bioactive agent may be selected to treat indications such as coronary artery angioplasty, renal artery angioplasty, carotid artery surgery, renal dialysis fistulae stenosis, or vascular graft stenosis.

The bioactive agent may be selected to perform one or more desired biological functions. For example, the abluminal surface of the medical device may comprise a bioactive agent selected to promote the ingrowth of tissue from the interior wall of a body vessel, such as a growth factor. An anti-angiogenic or antineoplastic bioactive agent such as paclitaxel, sirolimus, or a rapamycin analog, or a metalloproteinase inhibitor such as batimastaat may be coated on the medical device to mitigate or prevent undesired conditions in the vessel wall, such as restenosis. Many other types of bioactive agents can be coated on the medical device.

Bioactive agents for use in electrospinning solutions include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-.beta.

Medical devices comprising an antithrombogenic bioactive agent are particularly preferred for implantation in areas of the body that contact blood. For example, an antithrombogenic bioactive agent can be coated on the medical device surface. An antithrombogenic bioactive agent is any bioactive agent that inhibits or prevents thrombus formation within a body vessel. The medical device may comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor Vila and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethyl ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Also particularly preferred are solutions comprising a thrombolytic bioactive agent. Desirably, the thrombolytic bioactive agent is coated on the luminal surface of the medical device. Thrombolytic agents are used to dissolve blood clots that may adversely affect blood flow in body vessels. A thrombolytic agent is any therapeutic agent that either digests fibrin fibers directly or activates the natural mechanisms for doing so. The medical device can comprise any suitable thrombolytic agent. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA.

The configuration of the bioactive agent on the medical device will depend in part on the desired rate of elution for the bioactive agent(s). For example, bioactive agents may be incorporated in the medical device by: 1) mixing a bioactive agent with a solution prior to spinning the solution; 2) using two spinnerets to spin a polymer and a bioactive agent separately and simultaneously, 3) impregnating a spun polymer with a bioactive agent, and 4) electrospinning a solution over the top of a bioactive agent coated medical device.

In one example, a bioactive agent may be admixed with a solution comprising polymers and/or proteins. Electrospinning the resulting solution yields fibers that contain the desired bioactive agents. This method may be particularly suited to creating fibers that are not susceptible to being rejected by the body. Additionally, the fibers may later be melted, compressed, or otherwise manipulated, thereby changing or eliminating the interstices between the fibers, without reducing the drug content of the fibers.

In a second example, two spinnerets may be used in close proximity to each other, each having a common target. A first spinneret may be loaded with a solution comprising polymers and the second spinneret may be loaded with a solution comprising at least one bioactive agent. The spinnerets are charged and their solutions are spun simultaneously at the common target, creating a material that includes polymer fibers and bioactive agent fibers. The bioactive agent being fed into the second spinneret may also be mixed with a second polymer to improve the spin characteristics of the bioactive agent.

In another example, a solution may be electrospun onto a medical device incorporating a bioactive agent. For example, the medical device may be initially coated with a bioactive agent in any suitable manner. The medical device may then be coated by electrospinning a solution, such that the electrospun solution creates a non-woven network of fibers that at least partially overlays the bioactive agent previously deposited on the medical device. The bioactive agent may be deposited on the medical device in any suitable manner. For example, the coating may be deposited onto the medical device by spraying, dipping, pouring, pumping, brushing, wiping, ultrasonic deposition, vacuum deposition, vapor deposition, plasma deposition, electrostatic deposition, epitaxial growth, or any other suitable method.

The therapeutically effective amount of bioactive agent that is provided in connection with the various examples ultimately depends upon the condition and severity of the condition to be treated; the type and activity of the specific bioactive agent employed; the method by which the medical device is administered to the patient; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts.

Local administration of bioactive agents may be more effective when carried out over an extended period of time, such as a time period at least matching the normal reaction time of the body to an angioplasty procedure. At the same time, it may be desirable to provide an initial high dose of the bioactive agent over a preliminary period. For example, local administration of a bioactive agent over a period of days or even months may be most effective in treating or inhibiting conditions such as restenosis.

The polymeric fibers are nanofibers or microfibers. As set forth above, the first non-woven layer of fibers may include PET fibers, PTFE fibers, and ePTFE fibers. Most preferably, the first non-woven layer of fibers consists essentially of polyethylene terephthalate. The first non-woven layer of fibers may be deposited on the collection surface of a rotating mandrel, for example by electrospinning a PET solution according to one of the electrospinning techniques applied above. As set forth above, the PET solution may also include one or more bioactive agents.

The medical device also includes a first sol-gel layer at least partially over the first non-woven layer of fibers. This sol-gel layer may cover only a portion of the first non-woven layer of fibers or all of the first non-woven layer of fibers. In many stent graft applications, the first sol-gel layer will cover the entire PET fiber layer. As set forth above, the first sol-gel layer may also be applied in longitudinal bands or circumferential bands, or other geometries to the first non-woven layer of fibers.

The first sol-gel layer may be selected from the group comprising $SiO_2$, $TiO_2$, $Al_2O_3$, $ZrO_2$, $CeO_2$, $Fe_2O_3$, $BaTiO_3$, MgO, $SnO_2$, $B_2O_3$, $P_2O_5$, PbO, indium-tin-oxide, fluorine-doped tin oxide, antimony-doped tin oxide, zinc oxide, aluminum-zinc-oxide, and fluorine-zinc-oxide. In one example, the first sol-gel layer comprises at least two compounds. In one example, the first sol-gel layer consists essentially of two compounds. The first sol-gel layer of two or more compounds may be applied in varying ratios. In different examples, the first sol-gel layer may be applied in a ratio of ranging from 15:1 to 1:1, including 14:1, 13:1, 12:1; 11:1; 10:1, 9:1, 8:1, 7:1, 6:1, 5:1, 4:1, 3:1, 2:1 and 1:1. The ratio of also may vary along the length of the first non-woven layer of fibers. In a preferred example of the present invention, the ratio is about 9:1, varying somewhat between 11:1 and 7:1. In the most preferred example, the ratio is 9:1.

In one example, the first sol-gel layer may be selected from two or more compounds from the group comprising $SiO_2$, $TiO_2$, $Al_2O_3$, $ZrO_2$, $CeO_2$, $Fe_2O_3$, $BaTiO_3$, MgO, $SnO_2$, $B_2O_3$, $P_2O_5$, PbO, indium-tin-oxide, fluorine-doped tin oxide, antimony-doped tin oxide, zinc oxide, aluminum-zinc-oxide, and fluorine-zinc-oxide. In one example, the first sol-gel layer comprises $TiO_2$ and $SiO_2$. In a preferred example of the invention, the first sol-gel layer consists essentially of $TiO_2$ and $SiO_2$. Like the first non-woven layer of fibers, the first sol-gel layer may also include other agents that do not change the character and function of the sol-gel layer substantially. For example, the first sol-gel layer may comprise one or more bioactive agents.

As set forth above, the most preferred ratio of $TiO_2$:$SiO_2$ is 9:1. The ratio of $TiO_2$:$SiO_2$ can range from 15:1 to 1:1, including 14:1, 13:1, 12:1; 11:1; 10:1, 9:1, 8:1, 7:1, 6:1, 5:1, 4:1, 3:1, 2:1 and 1:1. The ratio also may vary along the length of the fiber layer. In a preferred example of the present invention, the ratio is about 9:1, varying somewhat between 11:1 and 7:1. In the most preferred example the ratio is 9:1.

The support structure also includes a second non-woven layer of fibers on the outer (abluminal) surface of the support structure. The second non-woven layer of fibers also includes polymeric fibers that are nanofibers or microfibers. The fiber material of the second non-woven layer of fibers may be the same or different than the fiber material of the first non-woven layer of fibers. Preferably however, the second non-woven layer of fibers consists essentially of polymeric fibers of the kind described above, and are preferably polyethylene terephthalate. The second non-woven layer of fibers may consists essentially or entirely of polyethylene terephthalate, or may include therapeutic or other bioactive agents as discussed above so long as the integrity of the fiber layer remains substantially uncomprised. The second non-woven layer of fibers may be applied by one of the electrospinning techniques applied above.

The present invention may be used to create an endoluminal prosthesis, such as a stent graft, for placement within a body vessel. The prosthesis may include a tubular body or a partially tubular body such as a bifurcated prosthesis. The prosthesis includes a support structure having a proximal end segment, a distal end segment, a lumen extending longitudinally within the support structure, a luminal surface, and an abluminal surface opposite the luminal surface. In a particular example, the prosthesis includes include a first sol-gel layer disposed partially or entirely on its luminal surface and abluminal surfaces, a first fiber layer disposed over the sol-gel layer on the luminal surface, and a second fiber layer disposed on the sol-gel layer on the abluminal surface of the support structure. For example, the support structure or stent may be first dipped or sprayed with a sol-gel solution, allowed to dry and then provided with one or more fiber layers over the sol-gel layers on either or both surfaces, and then further provided with a second sol-gel layer over one or more of the fiber layers. Various examples of the present invention for an endoluminal prosthesis are described below.

Figure 14:
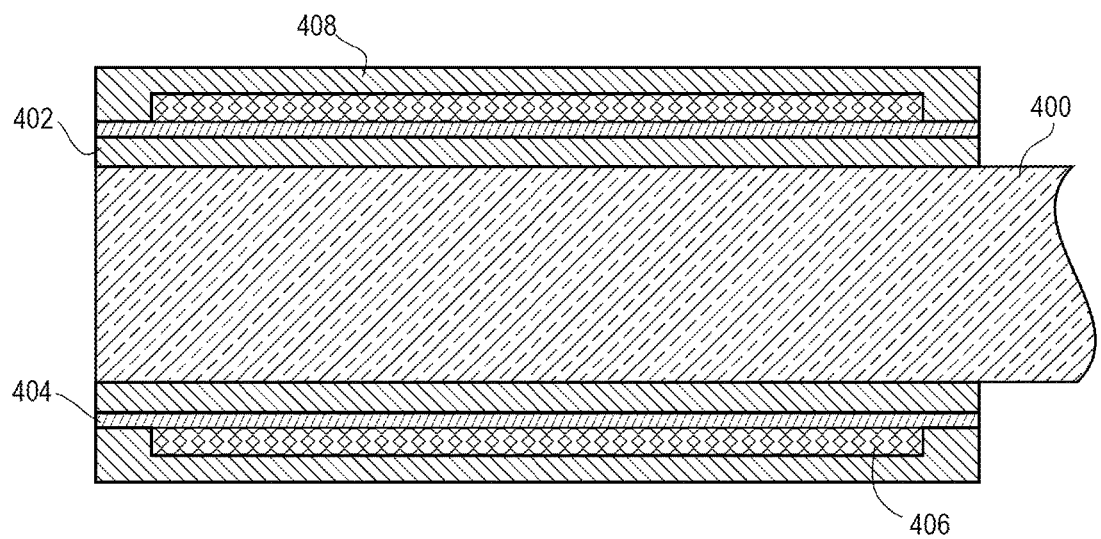
FIGS. 14 and 15 illustrate an example of a medical device encapsulated with two fiber layers using one sol-gel layer.
Figure 15:
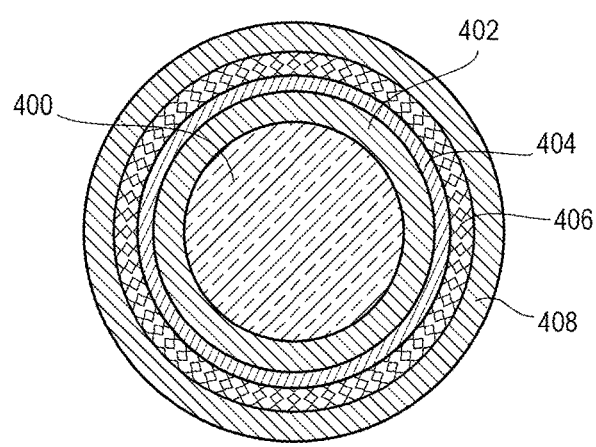

FIGS. 14 and 15 illustrate an example of a support structure encapsulated with two fiber layers using one sol-gel layer for improved adhesion. A first non-woven layer of fibers 402 is deposited on the mandrel 400. A first sol-gel layer 404 is then disposed over the fiber layer 402. The support structure 406, such as a tubular stent, is placed over the first sol-gel layer 404 that is at least partially over the first non-woven layer of fibers 402 as shown in FIGS. 14 and 15. In this manner, the first non-woven layer of fibers 402 may be positioned in contact with the luminal surface of the support structure 406. In other words, the first non-woven layer of fibers 402 may be contacted with the inner/luminal surface of the support structure 406 by locating the mandrel 400 at least partially within the lumen of the support structure 406. In one example, the support structure 406 may have a relaxed diameter and is placed over the first sol-gel layer 404 in an expanded state and then permitted to contract upon the first sol-gel layer 404.

The support structure 406 may be embedded in the first sol-gel layer 404 such that the first sol-gel layer 404 extends into one or more openings or interstices of the support structure 406. This may aid in encapsulating the support structure 406 within the graft body. An over-expanded support structure 406 may produce a radially inward force on the mandrel 400 and/or the first sol-gel layer 404. Such an inward force may aid in embedding the support structure 406 within the first sol-gel layer 404. A second non-woven layer of fibers 408 is then placed on the outer surface of the support structure 406. The second non-woven layer of fibers 408 may extend to the first sol-gel layer 404, if the support structure 406 does not cover the entirety of the first sol-gel layer 404. In other words, the second non-woven layer of fibers 408 may be partially in contact with the first sol-gel layer 404.

Figure 16:
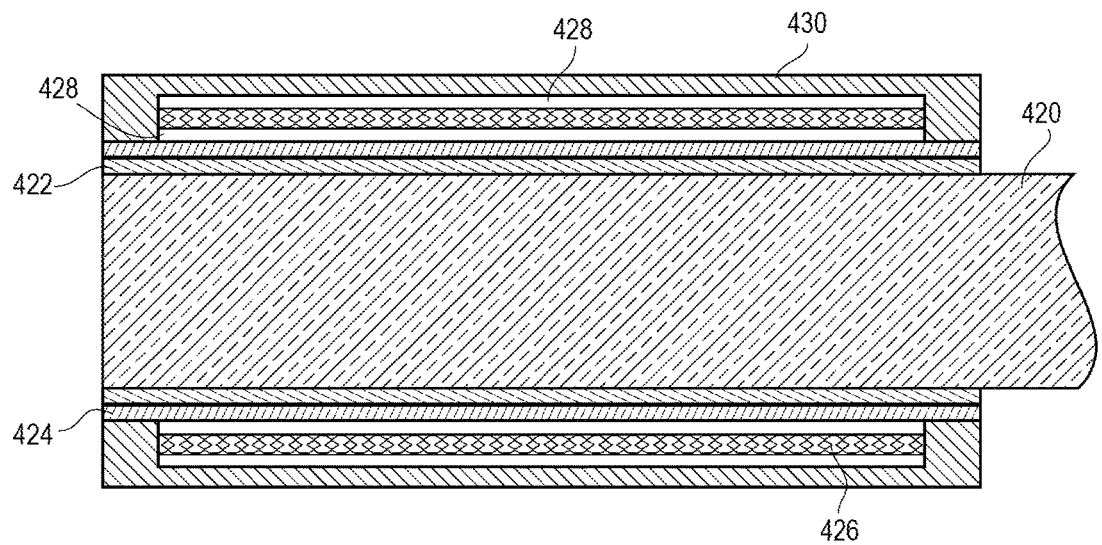
FIGS. 16 and 17 illustrate an example of a medical device encapsulated with two fiber layers using two sol-gel layers.
Figure 17:
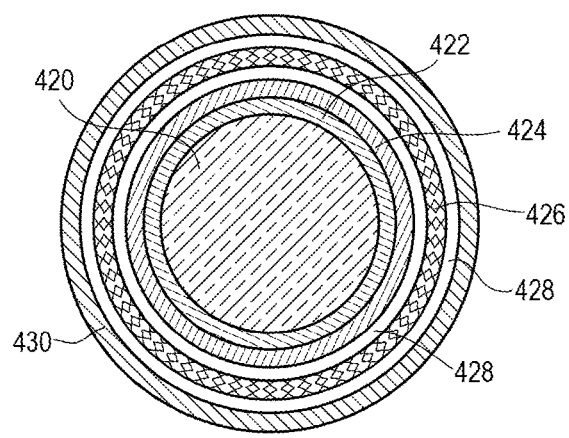

A method is provided for making an endoluminal prosthesis as shown in FIGS. 16 and 17 includes the steps of depositing a first fiber layer, for example by electrospinning a PET solution, onto a rotating mandrel; applying a first sol-gel layer, such as $TiO_2$/$SiO_2$ sol-gel at a desired ratio to the first layer; placing the support structure over the first sol-gel layer; depositing/electrospinning a second fiber layer over the support structure; and removing the encapsulated structure from the mandrel. The support structure may be dried following removal from the mandrel.

A further iteration of this method includes first soaking/dipping the support structure in a sol-gel to improve adhesion of the non-woven layers of fibers to the medical device. This method includes first soaking/dipping the support structure in a first sol-gel layer, for example a $SiO_2$ sol-gel, and allowing the first sol-gel to dry; depositing/electrospinning fibers onto a collection mandrel to form a first non-woven layer of fibers; applying a second sol-gel layer, such as $TiO_2/SiO_2$ sol-gel of a desired ratio, to the first non-woven layer of fibers; placing the support structure over the first non-woven layer of fibers/first sol-gel layer; depositing/electrospinning a second non-woven layer of fibers over the support structure; and removing the encapsulated structure from the mandrel. The support structure may be dried following removal from the mandrel.

This iteration provides a medical device that includes a support structure comprising a proximal end segment, a distal end segment, a lumen extending longitudinally within the support structure, a first surface, and second surface opposite the first surface. The medical device also includes a first sol-gel layer at least partially on the first surface and second surface. The medical device further includes a first non-woven layer of fibers at least partially over the first sol-gel layer. The medical device also includes a second sol-gel layer, different from the first sol-gel layer, at least partially over the first non-woven layer of fibers. The medical device also includes a second non-woven layer of fibers on the second surface of the support structure.

Figure 13B:
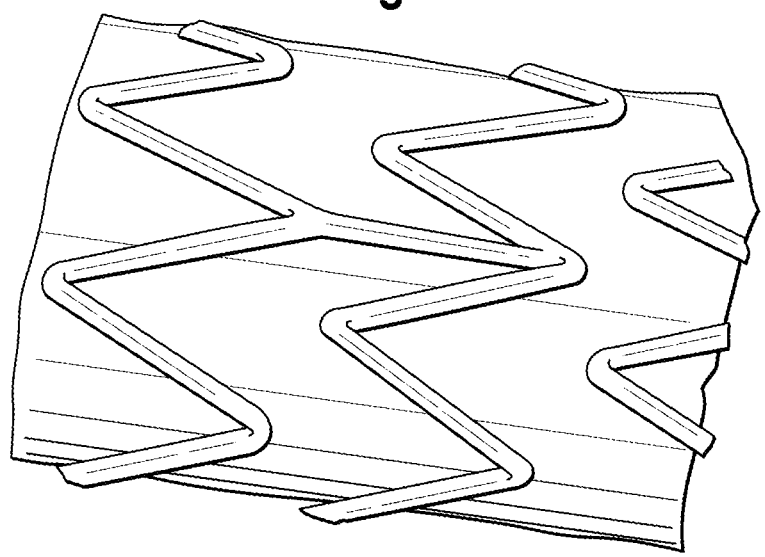
FIG. 13B illustrates an example of a stent soaked in a SiO₂ sol-gel layer.

In this improved adhesion example, the first sol-gel layer may be selected from the group comprising $SiO_2$, $TiO_2$, $Al_2O_3$, $ZrO_2$, $CeO_2$, $Fe_2O_3$, $BaTiO_3$, $MgO$, $SnO_2$, $B_2O_3$, $P_2O_5$, PbO, indium-tin-oxide, fluorine-doped tin oxide, antimony-doped tin oxide, zinc oxide, aluminum-zinc-oxide, and fluorine-zinc-oxide. In one example, the first sol-gel layer comprises silicon dioxide. The first sol-gel may consist essentially of silicon dioxide. FIG. 13B illustrates an example of a metallic medical device soaked in a silicon dioxide sol-gel layer.

Desirably, the first sol-gel layer includes at least two compounds. For example, the first sol-gel layer consists essentially of two compounds. The first sol-gel layer of two or more compounds may be applied in varying ratios. In different examples, the first sol-gel layer may be applied in a ratio in a range from 15:1 to 1:1, including 14:1, 13:1, 12:1; 11:1; 10:1, 9:1, 8:1, 7:1, 6:1, 5:1, 4:1, 3:1, 2:1 and 1:1. The ratio of also may vary along the length of the fiber layer. In a preferred example of the present invention, the ratio is about 9:1, varying somewhat between 11:1 and 7:1. In the most preferred example the ratio is 9:1.

In one example, the first non-woven layer of fibers comprises polymeric fibers. The polymeric fibers may be nanofibers or microfibers. In one example, the first non-woven layer of fibers comprises polyethylene terephthalate. In one example, the first non-woven layer of fibers consists essentially of polyethylene terephthalate. The first non-woven layer of fibers may be deposited on the collection surface of a rotating mandrel, for example by electrospinning a PET solution according to one of the electrospinning techniques applied above.

The second sol-gel layer may be different from the first sol-gel layer. In one example, the second sol-gel layer may be the same as the first-sol gel layer or it may include additional components.

The second non-woven layer of fibers may be different from the first non-woven layer of fibers or, the second non-woven layer of fibers may be of the same fibers as the first non-woven layer of fibers. The fibers of each of the layers may be the same or different sizes so long as they are nano micro fibers.

FIGS. 16 and 17 show an example of a support structure encapsulated with two fiber layers using two sol-gel layers for even further improved adhesion. A first non-woven layer of fibers 422 is deposited on a mandrel 420. A first sol-gel layer 424 is then disposed over the first non-woven layer of fibers 422. The support structure 426, such as a tubular stent, is placed over the first sol-gel layer 424 that is at least partially over the first non-woven layer of fibers 422 as shown in FIGS. 16 and 17. In this manner, the first non-woven layer of fibers 422 may be positioned in contact with the luminal surface of the support structure 426. In other words, the first non-woven layer of fibers 422 may be contacted with the inner/luminal surface of the support structure 426 by locating the mandrel 400 at least partially within the lumen of the support structure 426. In one example, the support structure 406 may have a relaxed diameter and is placed over the first sol-gel layer 424 in an expanded state and then permitted to contract upon the first sol-gel layer 424.

The support structure 426 may be embedded in the second sol-gel layer 428 such that the second sol-gel layer 428 extends into one or more openings or interstices of the support structure 426. This may aid in encapsulating the support structure 426 within the graft body. An over-expanded support structure 426 may produce a radially inward force on the mandrel 420 and/or the first sol-gel layer 424.

A second non-woven layer of fibers 430 is then placed on the second sol-gel layer 428. The second non-woven layer of fibers 430 may extend to the first sol-gel layer 424, if the support structure 426 does not cover the entirety of the first sol-gel layer 424.

FIGS. 18A, 18B, 18C, 19A, 19B, and 19C are illustrations of sheet materials made in accordance with the invention. An electrospun PET covering is created using sheet bonding from either roll-to-roll or flat plate fiber matrix and used to create a stent-graft or covered stent or other medical device. In an exemplary method, a desired thickness of fibers, such as PET fibers, is electrospun onto a collection apparatus to produce sheets of electrospun PET fibers. A $TiO_2/SiO_2$ sol-gel of varying ratios is applied, for example by spraying, dipping or the like, onto at least one side of the fiber sheet. In a different iteration, a tubular structure, such as a stent, may have been pre-soaked in a $SiO_2$ sol-gel and allowed to dry may be provided and a sheet of the fiber/sol-gel may be placed on either the luminal surface of the tubular structure, the abluminal surface of the tubular structure or both. Alternatively, a sheet of the material may be wrapped onto a mandrel, the tubular structure placed over the sheet, and a second sheet placed over the tubular structure to partially or entirely encapsulate the tubular structure. One or more sheets may be used on either or both surfaces. The use of sheets permits a covering method that can conform to a number of geometries of medical devices that are not tubular or cylindrical in nature.

In FIGS. 18A, 18B, and 18C, sheets are fibers are used to create a covered medical device. A first non-woven layer of fibers is electrospun onto at least a portion of a collection surface 500 of a medical plate to form a first non-woven fiber sheet 502. A first sol-gel layer 504 is then applied to at least a portion of the first non-woven fiber sheet 502. Subsequently, the first non-woven fiber sheet 502, with the first sol-gel layer 504, is removed from the collection surface 500, and placed over a portion of a support structure 506. Then, a second non-woven fiber sheet 508 may be deposited on at least a portion of the first sol-gel layer 504. In another example, the second non-woven fiber sheet 508 covers the entire first sol-gel layer 504. In one example, the second non-woven fiber sheet 508 is formed by electrospinning a layer of fibers onto the first sol-gel layer 504. In another example, the second non-woven fiber sheet 508 is formed on a collection surface like the collection surface 500 and then subsequently placed on the first sol-gel layer.

FIGS. 19A, 19B, and 19C show another example of when fiber sheets are used to create a covered medical device. In this example, a second sol-gel layer is first applied to the support structure 520. Then, the first non-woven fiber sheet 502, with the first sol-gel layer 504, is removed from the collection surface 500 of FIG. 18A, and placed over a portion of the second sol-gel layer 522. Then, a second non-woven fiber sheet 524 may be deposited on at least a portion of the first sol-gel layer 504. In another example, the second non-woven fiber sheet 524 covers the entire first sol-gel layer 504. In one example, the second non-woven fiber sheet 524 is formed by electrospinning a layer of fibers onto the first sol-gel layer 504. In another example, the second non-woven fiber sheet 508 is formed on a collection surface like the collection surface 500 of FIG. 18A and then subsequently placed on the first sol-gel layer.

The following examples are prophetic and are by way of example only and non-limiting.

Example 1

A stent is soaked in a $SiO_2$ sol-gel for approximately an hour at about 40° C. and air dried for about an hour at 60° C. Luminal passes of PET fibers are electrospun onto a collection mandrel. A $TiO_2/SiO_2$ sol-gel at a ratio of 9:1 is applied to the PET layer and the stent is placed on top of the PET $TiO_2/SiO_2$ layer. Abluminal passes of PET fibers are electrospun onto the abluminal surface of the stent on the mandrel, and the stent is removed from the mandrel. This may be accomplished using a soldering iron, ethanol, and a water bath, though other process are contemplated. The stent may then be dried at about 60° C. for about 15 minutes following removal. In this and the other examples, varying ratios of $TiO_2/SiO_2$ may be used. For example, the ratios may be from 1:1 to 15:1 $TiO_2/SiO_2$. Preferably, the ratio is about 9:1, encompassing a range of 7:1 to 11:1.

Example 2

Luminal passes of a PET fibers are electrospun onto a collection mandrel. A $TiO_2/SiO_2$ sol-gel at a ratio of 9:1 is applied to the PET layer and a stent is placed on top of the PET $TiO_2/SiO_2$ layer. Abluminal passes of PET fibers are electrospun onto the stent on the mandrel, and the stent is removed from the mandrel. This may be accomplished using a soldering iron, ethanol, and a water bath, though other process are contemplated. The stent may then be dried at about 60° C. for about 15 minutes following removal.

Example 3

A desired thickness of PET fibers is electrospun onto a collection apparatus such as a cylindrical mandrel, a flat plate, or a spool-to-spool take up system to produce sheets of electrospun PET. The thicknesses may vary based on the desired application. A $TiO_2/SiO_2$ sol-gel at a ratio of 9:1 is applied to the PET sheet to one or both sides. One or more layers are then assembled onto a medical device. For example, a sheet may be wrapped about the inner, outer or both inner and outer surfaces of a tubular construct. Alternatively, a sheet may be placed on a mandrel, a stent placed on top of the sheet, and a second sheet may be placed over the stent. The stent or medical device may be fully or partially encapsulated by the sheets.

Example 4

A desired thickness of PET fibers is electrospun onto a collection apparatus such as a cylindrical mandrel, a flat plate, or a spool-to-spool take-up system to produce sheets of electrospun PET fibers. The thicknesses may vary based on the desired application. For additionally improved adhesion, a medical device may be soaked in a $SiO_2$ sol-gel for approximately an hour at about 40° C. and air dried for about an hour at 60° C. A $TiO_2/SiO_2$ sol-gel at a ratio of 9:1 is applied to the PET sheet to one or both sides. One or more layers are then assembled onto a medical device. For example, a sheet may be wrapped about the inner, outer or both inner and outer surfaces of a tubular construct. Alternatively, a sheet may be placed on a mandrel, a stent placed on top of the sheet, and a second sheet may be placed over the stent. The stent or medical device may be fully or partially encapsulated by the sheets.

Example 5

A stent is soaked in a $SiO_2$ sol-gel for approximately an hour at about 40° C. and air dried for about an hour at 60° C. Luminal passes of PET fibers are electrospun onto a collection mandrel to create a layer approximately 20 μm thick. A $TiO_2/SiO_2$ sol-gel at a ratio of 9:1 is applied to the PET layer and a stent is placed on top of the PET $TiO_2/SiO_2$ layer. Abluminal passes of PET fibers are electrospun onto the stent on the mandrel to create a second layer of PET fibers about 20 μm thick, and the stent is removed from the mandrel. This may be accomplished using a soldering iron, ethanol, and a water bath, though other process are contemplated. The stent may then be dried at about 60° C. for about 15 minutes following removal. In this and the other examples, varying ratios of $TiO_2/SiO_2$ may be used. For example, the ratios may be from 1:1 to 15:1 $TiO_2/SiO_2$. Preferably, the ratio is about 9:1, encompassing a range of 7:1 to 11:1.

Example 6

Luminal passes of a PET fibers are electrospun onto a collection mandrel to create an electrospun layer of about 20 μm thick. A $TiO_2/SiO_2$ sol-gel at a ratio of 9:1 is applied to the PET layer and a stent is placed on top of the PET $TiO_2/SiO_2$ layer. Abluminal passes of PET fibers are electrospun onto the stent on the mandrel to create a second layer of PET fibers about 20 μm thick, and the stent is removed from the mandrel. This may be accomplished using a soldering iron, ethanol, and a water bath, though other process are contemplated. The stent may then be dried at about 60° C. for about 15 minutes following removal.

Example 7

PET fibers of about 20 μm thick are electrospun onto a collection apparatus such as a cylindrical mandrel, a flat plate, or a spool-to-spool take up system to produce sheets of electrospun PET. A $TiO_2/SiO_2$ sol-gel at a ratio of 9:1 is applied to the PET sheet to one or both sides. One or more layers are then assembled onto a medical device. For example, a sheet may be wrapped about the inner, outer or both inner and outer surfaces of a tubular construct. Alternatively, a sheet may be placed on a mandrel, a stent placed on top of the sheet, and a second sheet may be placed over the stent. The stent or medical device may be fully or partially encapsulated by the sheets.

Example 8

PET fibers of about 20 μm thick are electrospun onto a collection apparatus such as a cylindrical mandrel, a flat plate, or a spool-to-spool take-up system to produce sheets of electrospun PET fibers. For additionally improved adhesion, a medical device may be soaked in a $SiO_2$ sol-gel for approximately an hour at about 40° C. and air dried for about an hour at 60° C. A $TiO_2/SiO_2$ sol-gel at a ratio of 9:1 is applied to the PET sheet to one or both sides. One or more layers are then assembled onto a medical device. For example, a sheet may be wrapped about the inner, outer or both inner and outer surfaces of a tubular construct. Alternatively, a sheet may be placed on a mandrel, a stent placed on top of the sheet, and a second sheet may be placed over the stent. The stent or medical device may be fully or partially encapsulated by the sheets.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

What is claimed is:

1. A medical device for treating a body vessel, comprising:
    a tubular support structure having a lumen extending longitudinally through the tubular support structure, a luminal surface, and an abluminal surface opposite the luminal surface;
    a first sol-gel layer disposed at least partially on the luminal surface of the tubular support structure;
    at least one first non-woven layer of polymeric fibers disposed at least partially over the first sol-gel layer; and
    at least one second non-woven layer of polymeric fibers disposed at least partially on the abluminal surface of the tubular support structure,
    wherein the first sol-gel layer comprises $TiO_2$ and $SiO_2$ and wherein the ratio of $TiO_2$ and $SiO_2$ is from 11:1 $TiO_2:SiO_2$ to 7:1 $TiO_2:SiO_2$.

2. The medical device of claim 1, wherein the first sol-gel layer has a ratio of 9 to 1 $TiO_2:SiO_2$.

3. The medical device of claim 1, wherein the first sol-gel layer has a ratio of 8 to 1 $TiO_2:SiO_2$.

4. The medical device of claim 1, wherein the first sol-gel layer consists essentially of $TiO_2$ and $SiO_2$.

5. The medical device of claim 1, wherein fibers of the polymeric fibers sheets are selected from the group consisting of poly(urethanes), poly(siloxanes), silicones, poly(ethylene), poly(vinyl pyrrolidone), polyethylene terephthalate, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polytetrafluoroethylene (PTFE), polyorthoesters, and combinations thereof.

6. The medical device of claim 1, wherein the polymeric fibers are selected from the group consisting of polyethylene terephthalate, polytetrafluoroethylene (PTFE), expanded polytetrafluoroethylene (ePTFE), and mixtures thereof.

7. The medical device of claim 1, wherein the medical device further comprises a second sol-gel layer coated at least partially on the abluminal surface of the tubular support structure.

8. The medical device of claim 7, wherein the second sol-gel layer is selected from the group consisting of $TiO_2$, $Al_2O_3$, $ZrO_2$, $CeO_2$, $Fe_2O_3$, $BaTiO_3$, $MgO$, $SnO_2$, $B_2O_3$, $P_2O_5$, $PbO$, silicon dioxide, indium-tin-oxide, fluorine-doped tin oxide, antimony-doped tin oxide, zinc oxide, aluminum-zinc-oxide, and fluorine-zinc-oxide.

9. The medical device of claim 8, wherein the second sol-gel layer comprises silicon dioxide.

10. A medical device comprising:
    a support structure having a lumen extending longitudinally through the support structure, a luminal surface, and an abluminal surface opposite the luminal surface;
    a first sol-gel layer on the luminal surface of the support structure and a second sol-gel layer on the abluminal surface of the support structure wherein the first sol-gel layer consists essentially of $TiO_2$ and $SiO_2$ in a ratio from 11:1 $TiO_2:SiO_2$ to 7:1 $TiO_2:SiO_2$;
    a first sheet of non-woven polymeric fibers disposed at least partially over the first sol-gel layer on the luminal surface of the support structure; and
    a second sheet of non-woven polymeric fibers disposed at least partially over the second sol-gel layer on the abluminal surface of the support structure.

11. The medical device of claim 10, wherein the fiber sheets comprise nanofibers or microfibers of polyethylene terephthalate.

12. The medical device of claim 10, wherein the ratio of $TiO_2$ and $SiO_2$ is from 9 to 1 $TiO_2:SiO_2$ and the second sol-gel layer comprises silicon dioxide.

13. A medical device for treating a medical device, the medical device comprising:
    a support structure comprising a lumen extending longitudinally through the support structure, a luminal surface, and an abluminal surface opposite the luminal surface;
    a first sol-gel layer on the luminal surface of the support structure and a second sol-gel layer on the abluminal surface of the support structure, the first sol-gel layer consists essentially of $TiO_2$ and $SiO_2$ in a ratio of from 11:1 $TiO_2:SiO_2$ to 7:1 $TiO_2:SiO_2$;
    a first non-woven layer of polymeric fibers disposed at least partially over the first sol-gel layer on the luminal surface of the support structure; and
    a second non-woven layer of polymeric fibers disposed at least partially over the second sol-gel layer on the abluminal surface of the support structure.

14. The medical device of claim 13, wherein the second sol-gel layer is disposed at least partially on both of the luminal surface and the abluminal surface of the tubular support structure such that a portion of the second sol-gel layer is in contact with the first sol-gel layer and the second non-woven layer of polymeric fibers.

15. The medical device of claim 14, wherein the second sol-gel layer comprises silicon dioxide.

16. A medical device for treating a body vessel, comprising:
    a tubular support structure having a lumen extending longitudinally through the tubular support structure, a luminal surface, and an abluminal surface opposite the luminal surface;
    a first sol-gel layer disposed at least partially on the luminal surface of the tubular support structure;

at least one first non-woven layer of polymeric fibers disposed at least partially over the first sol-gel layer; and at least one second non-woven layer of polymeric fibers disposed at least partially on the abluminal surface of the tubular support structure, wherein the first sol-gel layer consists essentially of $TiO_2$ and $SiO_2$ in a ratio of 9 to 1 $TiO_2$:$SiO_2$.

17. A medical device for treating a body vessel, comprising:

a tubular support structure having a lumen extending longitudinally through the tubular support structure, a luminal surface, and an abluminal surface opposite the luminal surface;

a first sol-gel layer disposed at least partially on the luminal surface of the tubular support structure;

a second sol-gel layer coated at least partially on the abluminal surface of the tubular support structure at least one first non-woven layer of polymeric fibers disposed at least partially over the first sol-gel layer; and at least one second non-woven layer of polymeric fibers disposed at least partially on the abluminal surface of the tubular support structure, wherein the first sol-gel layer comprises $TiO_2$ and $SiO_2$ in a ratio of 9 to 1 $TiO_2$:$SiO_2$ and the second sol-gel layer comprises silicon dioxide.

18. A medical device for treating a body vessel, comprising:

a tubular support structure having a lumen extending longitudinally through the tubular support structure, a luminal surface, and an abluminal surface opposite the luminal surface;

a first sol-gel layer disposed at least partially on the luminal surface of the tubular support structure;

a second sol-gel layer coated at least partially on the abluminal surface of the tubular support structure at least one first non-woven layer of polymeric fibers disposed at least partially over the first sol-gel layer; and at least one second non-woven layer of polymeric fibers disposed at least partially on the abluminal surface of the tubular support structure, wherein the first sol-gel layer consists essentially of $TiO_2$ and $SiO_2$ in a ratio of 9 to 1 $TiO_2$:$SiO_2$ and the second sol-gel layer comprises silicon dioxide.

* * * * *